US012702279B2

(12) United States Patent
Mingione et al.

(10) Patent No.: US 12,702,279 B2
(45) Date of Patent: Aug. 11, 2026

(54) STEERABLE SHEATH AND ADJUSTABLE SCOPE ATTACHMENT

(71) Applicant: JOHNSON & JOHNSON ENTERPRISE INNOVATION, INC., New Brunswick, NJ (US)

(72) Inventors: Louis Mingione, Madison, WI (US); Daniel Price, Madison, WI (US); Kevin Royalty, Madison, WI (US); Jeffrey Bissing, Madison, WI (US); Samantha Weber, Madison, WI (US); Nathan Clemans, Madison, WI (US); Laura Wiley, Madison, WI (US); Nathan Wallace, Madison, WI (US); Eric Bielefeld, Madison, WI (US)

(73) Assignee: Johnson & Johnson Enterprise Innovation Inc., New Brunswick, NJ (US)

(*) Notice: Subject to any disclaimer, the term of this patent is extended or adjusted under 35 U.S.C. 154(b) by 1048 days.

(21) Appl. No.: 17/578,109

(22) Filed: Jan. 18, 2022

(65) Prior Publication Data

US 2023/0225595 A1 Jul. 20, 2023

(51) Int. Cl.

| | |
|---|---|
| ***A61B 1/005*** | (2006.01) |
| ***A61B 1/00*** | (2006.01) |
| ***A61B 1/018*** | (2006.01) |
| ***A61B 1/267*** | (2006.01) |

(52) U.S. Cl.

CPC ........ *A61B 1/0052* (2013.01); *A61B 1/00133* (2013.01); *A61B 1/0057* (2013.01); *A61B 1/018* (2013.01); *A61B 1/2676* (2013.01)

(58) Field of Classification Search

None

See application file for complete search history.

(56) References Cited

U.S. PATENT DOCUMENTS

| | | | |
|---|---|---|---|
| D444,488 | S | 7/2001 | Selic et al. |
| D449,057 | S | 10/2001 | Selic et al. |
| D616,477 | S | 5/2010 | Long et al. |
| D616,909 | S | 6/2010 | Long |
| D624,104 | S | 9/2010 | Miyake et al. |

(Continued)

FOREIGN PATENT DOCUMENTS

| | | | |
|---|---|---|---|
| CN | 308008930 | S | 4/2023 |
| DE | 19933278 | A1 | 1/2001 |

(Continued)

OTHER PUBLICATIONS

Written Opinion and International Search Report from corresponding PCT Application No. PCT/IB2023/050405 mailed Mar. 27, 2023.

(Continued)

*Primary Examiner* — Jay B Shah

(74) *Attorney, Agent, or Firm* — Vorys, Sater, Seymour and Pease LLP

(57) ABSTRACT

A system comprising an adjustable mount arm, a bronchoscope coupled to the adjustable mount arm, an attachment coupled to the bronchoscope, and a steerable sheath coupled to the attachment and configured to be inserted through the bronchoscope. The system further includes a flexible probe configured to be inserted through the steerable sheath and the bronchoscope.

20 Claims, 25 Drawing Sheets

(56) References Cited

U.S. PATENT DOCUMENTS

| | | | |
|---|---|---|---|
| D629,030 S | 12/2010 | Long et al. | |
| D636,419 S | 4/2011 | Nakagiri et al. | |
| D636,803 S | 4/2011 | Nakagiri et al. | |
| D690,753 S | 10/2013 | Liu et al. | |
| D693,921 S | 11/2013 | Burton et al. | |
| D705,422 S | 5/2014 | Burton et al. | |
| D747,800 S | 1/2016 | Dunleavy et al. | |
| D778,971 S | 2/2017 | Long et al. | |
| D827,819 S | 9/2018 | Hillukka et al. | |
| D843,656 S | 3/2019 | Zhang et al. | |
| D911,408 S | 2/2021 | Okada et al. | |
| D912,117 S | 3/2021 | Berkowitz et al. | |
| D915,487 S | 4/2021 | Sell | |
| D928,210 S | 8/2021 | Graessle | |
| D946,068 S | 3/2022 | Endo et al. | |
| D970,015 S | 11/2022 | Cha et al. | |
| D974,557 S | 1/2023 | Behrendt et al. | |
| D979,623 S | 2/2023 | Cao | |
| D993,412 S | 7/2023 | Karim | |
| 2011/0088498 A1* | 4/2011 | Ettwein | A61M 25/0136 74/479.01 |
| 2012/0116396 A1* | 5/2012 | Price | H02J 7/0044 606/45 |
| 2014/0012075 A1 | 1/2014 | Konstorum | |
| 2015/0301096 A1 | 10/2015 | Dresher | |
| 2016/0192919 A1 | 7/2016 | Horii | |
| 2019/0111238 A1 | 4/2019 | Schultz et al. | |
| 2019/0246876 A1 | 8/2019 | Schaning | |
| 2019/0298321 A1* | 10/2019 | Intintoli | A61B 1/07 |
| 2021/0379332 A1 | 12/2021 | Komp et al. | |
| 2022/0160440 A1 | 5/2022 | Jaramaz et al. | |
| 2023/0108741 A1 | 4/2023 | Kawakami et al. | |

FOREIGN PATENT DOCUMENTS

| | | |
|---|---|---|
| EP | 1046406 A2 | 10/2000 |
| EP | 0090887500001 | 9/2022 |
| EP | 0090891390001 | 9/2022 |
| GB | 6219662 S | 9/2022 |
| WO | D053082001 | 11/2000 |
| WO | 2021108562 A1 | 6/2021 |

OTHER PUBLICATIONS

Ambu aScope 3 Slim 3.8/1.2. Retrieved from the internet Aug. 10, 2023. 2 pages.

Auris Monarch Robotic Bronchoscopes. Retrieved from the internet Aug. 10, 2023. 14 pages.

BodyVision : LungVision. Http://www.bodyvisionmedical.com/ Retrieved from the internet Aug. 10, 2023. 18 pages.

CARTO VIZIGO® Bi-Directional Guiding Sheath. Retrieved from the internet Aug. 10, 2023. 9 pages.

Intuitive lon Robotic Bronchoscopes. Retrieved from the internet Aug. 10, 2023. 8 pages.

Olympus Hybrid Bronchoscope BF-MP190F. Retrieved from the internet Aug. 10, 2023. 3 pages.

Pentax Medical. Pediatric/periphery Bronchoscopes. Pentax EB-1170k, EB-1570k, EB-1970k, EB-1970tk. Retrieved from the internet Aug. 10, 2023. 34 pages.

SuperDimension. www.Medtronic.com. Retrieved from the internet Aug. 10, 2023. 5 pages.

Veran Medical. www.veranmedical.com . Retrieved from the internet Aug. 10, 2023. 2 pages.

Abhinay PV, "Industrial Robot Arm Model DOF-6", 3D CAD Model Library, Retrieved from https://grabcad.com/library/industrial-robot-arm-model-dof-6-1, Jul. 28, 2021, 2 pages.

"Noga NF60003 Articulated Arm Type, 6mm Shank Diameter, 4.2" Length Indicator Holder Rod, Travers Tool, Retrieved from https://www.travers.com/product/noga-nf60003-indicator-holder-rod-99-001-056, Aug. 7, 2023, 2 pages.

"RadiaTM: Bidirectional Steerable Diagnostic Catheter", Boston Diagnostic, Retrieved from https://www.bostonscientific.com/en-us/products/catheters--diagnostic/radia.html, Jan. 15, 2015, 2 pages.

"Stryker Steerable Introducer Sheath", Stryker, Retrieved from https://www.stryker.com/us/en/portfolios/medical-surgical-equipment/steerable-introducer-sheath.html, Jan. 31, 2023, 2 pages.

* cited by examiner 266
514
386
382
558
402
522
554
550
538
378
530
526
410
534
418
390

266
390
418
542
410
546
550
530
526
518
378
522
402
386
502
524

STEERABLE SHEATH AND ADJUSTABLE SCOPE ATTACHMENT

TECHNICAL FIELD

The present disclosure relates to endoscope accessories, and more particularly to bronchoscope accessories. The devices described herein find use in a variety of endoscopy (e.g., bronchoscopy) applications.

BACKGROUND

Precise placement of catheters, probes, and other tools is important in many medical procedures. For example, precise placement of an ablation probe is important for transbronchial lung ablation or local drug delivery. Robotic systems can help with precision placement but are often cost prohibitive. Medical procedures with conventional endoscopic systems involve several devices and a single user has difficulty holding and manipulating all the devices in the conventional system.

SUMMARY

The disclosure provides, in one aspect, a bronchoscope attachment including a mount with a port, and a cradle defining an insertion axis. The insertion axis is aligned with the port. The bronchoscope attachment further includes a linkage positioned between the mount and the cradle. The linkage is movable between a first position in which the cradle is positioned a first distance from the port and the insertion axis is aligned with the port; and a second position in which the cradle is positioned a second distance from the port and the insertion axis is aligned with the port.

In some embodiments, the insertion axis remains aligned with the port in response to movement of the linkage.

In some embodiments, the linkage includes a first arm, a second arm, and an elbow coupled between the first arm and the second arm.

In some embodiments, a first end of the first arm is pivotably coupled to the mount, and a second end of the first arm is pivotably coupled to the elbow.

In some embodiments, a first end of the second arm is coupled to the cradle, and a second end of the second arm is pivotably coupled to the elbow.

In some embodiments, the elbow includes a first gear coupled to the first arm and a second gear coupled to the second arm.

In some embodiments, the first gear is enmeshed with the second gear.

In some embodiments, the first arm includes a first link and a second link, and the second arm includes a third link and a fourth link.

In some embodiments, the second link and the third link are rotatably coupled together by a gear set positioned in the elbow.

In some embodiments, the second arm moves in response to movement of the first arm and the first arm moves in response to movement of the second arm.

In some embodiments, the linkage is a telescopic slide.

In some embodiments, the mount includes a base portion, a door, and a latch.

In some embodiments, the mount includes a first opening partially defined by the door and a second opening at least partially defined by the door, wherein the first opening is aligned with the second opening.

In some embodiments, the port is formed in the base portion.

In some embodiments, the door is movable with respect to the base portion between an open position and a closed position.

In some embodiments, the cradle remains in place in response to the door moving to the open position.

In some embodiments, the latch is actuated to lock the door in the closed position.

In some embodiments, the bronchoscope attachment further includes a seal coupled to the port.

In some embodiments, the mount is rotatable with respect to a bronchoscope.

In some embodiments, the port remains in position as the mount rotates about the port.

The disclosure provides, in one aspect, a steerable sheath including a handle with a housing, a port formed on the housing, and a user input wheel rotatably coupled to the housing. The steerable sheath further includes a sheath extending from the handle. The sheath includes a proximal end coupled to the handle and a distal end. The steerable sheath includes a transmission coupled between the user input wheel and the distal end of the sheath, and actuation of the user input wheel articulates the distal end of the sheath.

In some embodiments, the distal end is curved at an angle with the user input wheel in a neutral position.

In some embodiments, the steerable sheath further includes a detent positioned within the housing. The detent engages the transmission with the user input wheel in the neutral position.

In some embodiments, the angle is 70°.

In some embodiments, the user input wheel includes a first indicator visible when the user input wheel is in the neutral position and a second indicator visible when the user input wheel is in a non-neutral position.

In some embodiments, the steerable sheath further includes a braking assembly that adjusts the amount of frictional engagement between the housing and the user input wheel.

In some embodiments, the user input wheel includes a hub positioned around a boss formed on the housing, and the braking assembly includes a sleeve positioned around the boss. The braking assembly further includes a spring washer positioned between the sleeve and the hub, and a fastener to secure the sleeve to the boss. The sleeve is adjustably positioned relative to the hub, and the braking assembly holds the position of the user input wheel when the user input wheel is released by a user.

In some embodiments, the port is connected to the sheath, and wherein an obturator is inserted through the port.

In some embodiments, the user input wheel rotates about an axis, and the axis intersects a sheath axis. A longitudinal axis of the handle is aligned with the sheath axis.

In some embodiments, the handle includes a circumferential groove on an external surface of the housing, and the housing includes a tapered end. The proximal end of the sheath is coupled to the tapered end.

In some embodiments, the transmission includes a drive gear, a belt coupled between the user input wheel and the drive gear, a first rack enmeshed with the drive gear, a second rack enmeshed with the drive gear, and a first pull wire coupled to the first rack. Actuation of the first pull wire articulates the distal end of the sheath.

In some embodiments, the transmission further includes a second pull wire coupled to the second rack, and wherein actuation of the second pull wire articulates the distal end of the sheath.

In some embodiments, the first rack and the second rack translate relative to the drive gear in response to rotation of the user input wheel. In some embodiments, the housing includes a first slot that at least partially receives the first rack and a second slot that at least partially receives the second rack, such that the first rack and the second rack are slidable with respect to the housing.

In some embodiments, the user input wheel is positioned within the handle with a first exposed portion and a second exposed portion, and the housing is positioned between the first exposed portion and the second exposed portion.

In some embodiments, the user input wheel is rotatably coupled to the housing about an axis aligned with a longitudinal axis of the housing, and the user input wheel is an actuation ring.

In some embodiments, the user input wheel is spaced from a proximal end of the housing.

In some embodiments, the transmission includes a linkage coupled to the user input wheel with a pin and a spiral slot. The linkage translates linearly in response to rotation of the user input wheel.

In some embodiments, the transmission includes a planetary gear assembly and a power screw.

In some embodiments, the transmission includes a pawl.

In some embodiments, the transmission includes at least one electrical component, wherein the electrical component is a sensor, an actuator, a power source, or a controller.

The disclosure provides, in one aspect, a system including an adjustable mount arm, a bronchoscope coupled to the adjustable mount arm, an attachment coupled to the bronchoscope, and a steerable sheath coupled to the attachment and configured to be inserted through the bronchoscope.

In some embodiments, the system further includes a flexible probe configured to be inserted through the steerable sheath and the bronchoscope.

In some embodiments, the flexible probe is a microwave ablation probe.

In some embodiments, the system further includes a local drug delivery device configured to be inserted through the steerable sheath and bronchoscope.

In some embodiments, the attachment includes a mount with a port, and a cradle defining an insertion axis. The insertion axis is aligned with the port. The attachment further includes a linkage positioned between the mount and the cradle. The linkage is movable between a first position in which the cradle is positioned a first distance from the port and the insertion axis is aligned with the port; and a second position in which the cradle is positioned a second distance from the port and the insertion axis is aligned with the port.

In some embodiments, the port on the mount receives a port formed on the bronchoscope.

In some embodiments, the mount includes a first opening, and a second opening aligned with the first opening; and the bronchoscope extends through the first opening and the second opening.

In some embodiments, the steerable sheath is releasably coupled to the cradle.

In some embodiments, the steerable sheath includes a handle including a housing, a port formed on the housing, and a user input wheel rotatably coupled to the housing. The steerable sheath further includes a sheath extending from the handle. The sheath includes a proximal end coupled to the handle and a distal end. The steerable sheath further includes a transmission coupled between the user input wheel and the distal end of the sheath. Actuation of the user input wheel articulates the distal end of the sheath.

Other aspects of the disclosure will become apparent by consideration of the detailed description and accompanying drawings.

BRIEF DESCRIPTION OF THE DRAWINGS

The accompanying figures and examples are provided by way of illustration and not by way of limitation. The foregoing aspects and other features of the disclosure are explained in the following description, taken in connection with the accompanying example figures (also "FIG.") relating to one or more embodiments.

Figure 1:
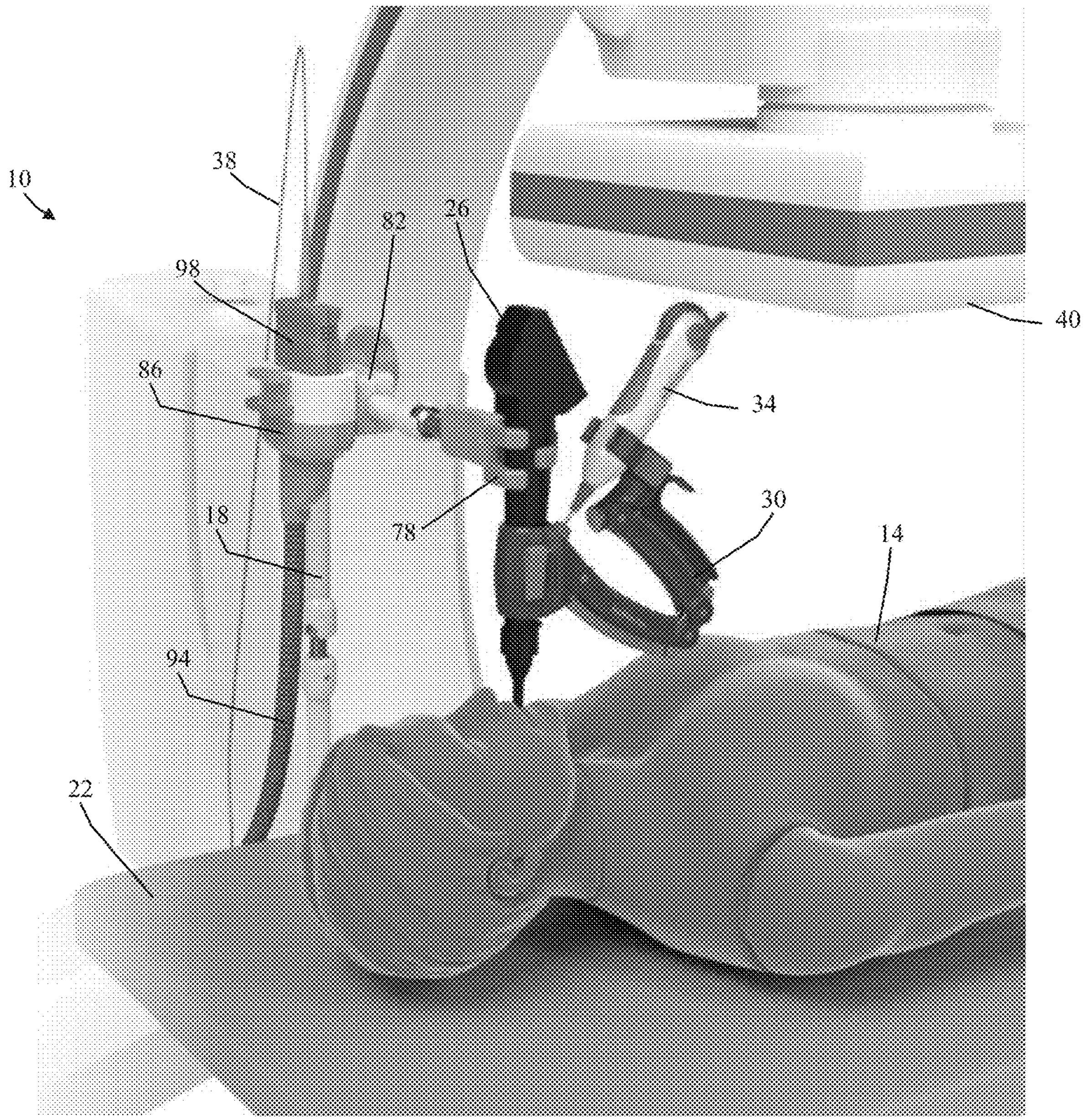
FIG. 1 is a perspective view of a system for use in an endoscopic procedure.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Coupled" as used herein refers to two or more components that are secured, by any suitable means, together. Accordingly, in some embodiments, the statement that two or more parts or components are "coupled" shall mean that the parts are joined or operate together either directly or indirectly, e.g., through one or more intermediate parts or components.

"Removably coupled" as used herein means that one component is coupled with another component in an essentially temporary manner. That is, the two components are coupled in such a way that the joining or separation of the components is easy and does not damage the components. Accordingly, "removably coupled" components may be readily uncoupled and recoupled without damage to the components.

"Operatively coupled" as used herein means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

Therapeutic endoscopy or interventional endoscopy pertains to an endoscopic procedure during which a treatment (e.g., tissue ablation) (e.g., tissue collection) is carried out via the endoscope. This contrasts with diagnostic endoscopy, where the aim of the procedure is purely to visualize an internal part of a body (e.g., gastrointestinal region, respiratory region, urinary tract region, etc.) in order to aid diagnosis. In practice, a procedure which starts as a diagnostic endoscopy may become a therapeutic endoscopy depending on the findings.

Generally, therapeutic endoscopy involves the administration of an endoscope ("primary catheter") into a body region until a natural stopping positioning is reached (e.g., until the circumference of the body region inhibits further advancement of the endoscope). Next, a flexible sheath having a circumference smaller than the circumference of the endoscope is advanced through the endoscope and to a desired body region location. Next, a therapeutic or diagnostic tool (e.g., an ablation energy delivery tool) (e.g., a tissue collection tool) (e.g., biopsy needle) having a circumference smaller than the diameter of the flexible sheath is advanced through the flexible sheath to the desired body region location. Next, ablation energy is delivered to the desired body region location. Upon completion of the therapeutic endoscopy, the ablation energy delivery tool is withdrawn through the flexible sheath, the flexible sheath is withdrawn through the endoscope, and the endoscope is withdrawn from the subject.

With reference to FIG. 1, a system 10 for performing an endoscopic procedure on a patient 14 is illustrated. The system 10 includes an adjustable mount arm 18 coupled to a patient bed 22, and a bronchoscope 26 coupled to the adjustable mount arm 18. An attachment 30 (i.e., a bronchoscope attachment, a support arm) is coupled to the bronchoscope 26 and a steerable sheath 34 is coupled to the attachment 30. As described in greater detail herein, the steerable sheath 34 is configured to be inserted through the bronchoscope 26 and a flexible probe 38 (e.g., a microwave ablation probe) is configured to be inserted through the steerable sheath 34 and the bronchoscope 26. In some embodiments, a medical imaging device 40 (e.g., X-ray, fluoroscopy, CT, etc.) is utilized with the system 10 to aid positioning of the bronchoscope 26, the steerable sheath 34, and the flexible probe 38 within the patient 14. Although the system 10 is illustrated with a bronchoscope 26, the systems disclosed herein can be utilized with any type of endoscope or "scope."

Figure 2:
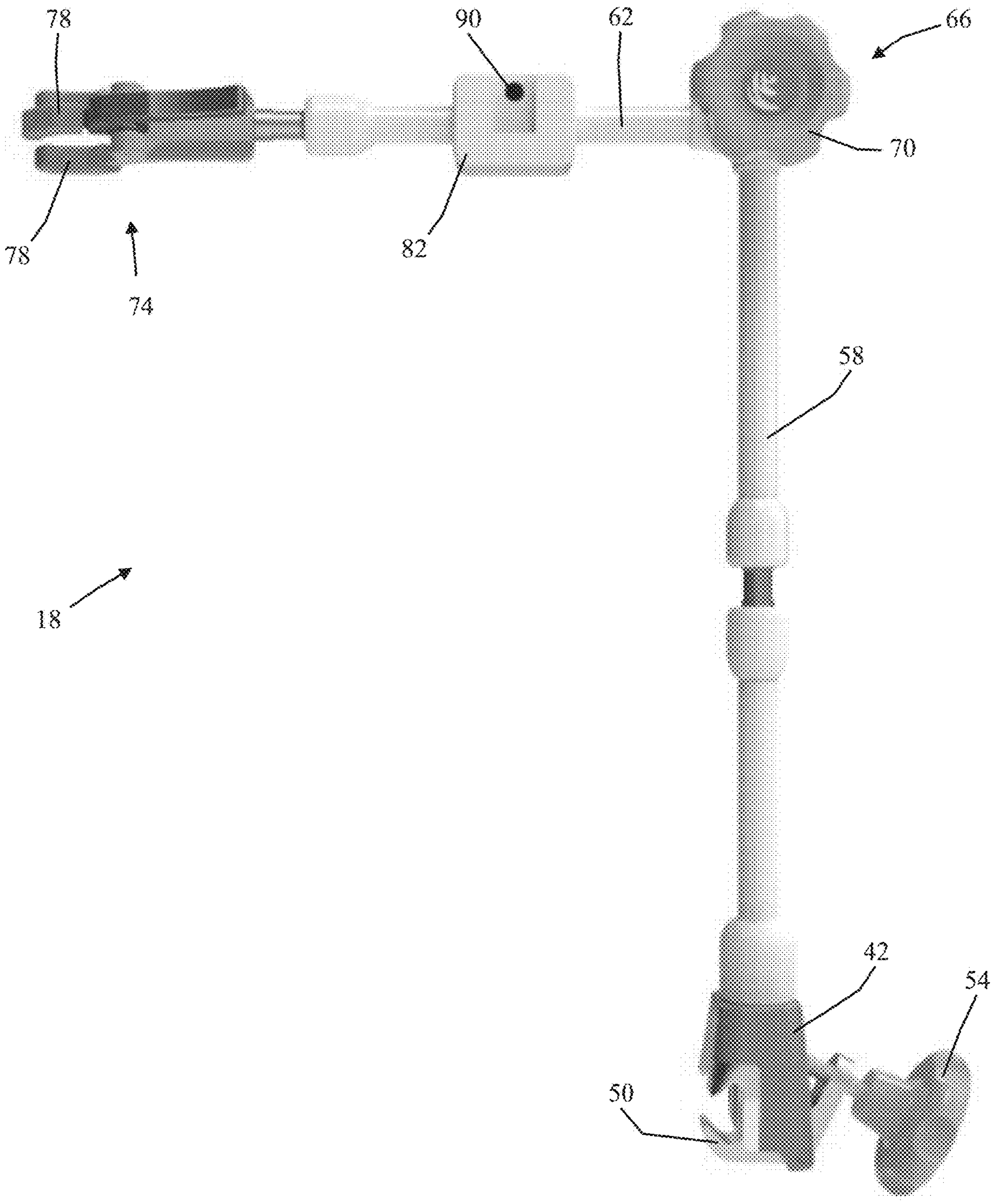
FIG. 2 is a side view of an adjustable mount arm.
Figure 3:
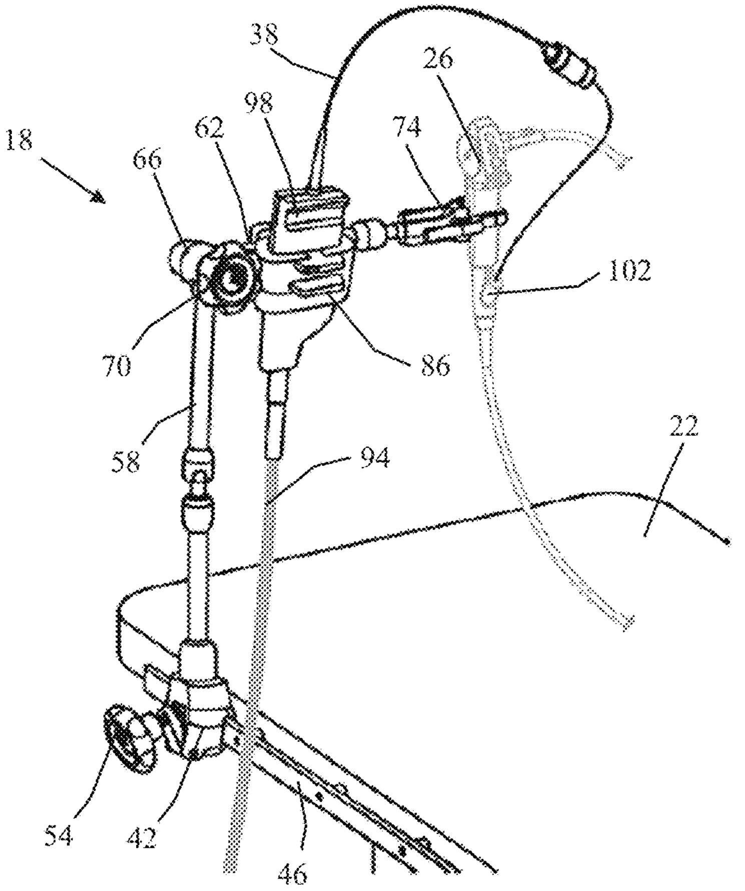
FIG. 3 is a perspective view of a system for use in an endoscopic procedure.

With reference to FIGS. 2 and 3, the adjustable mount arm 18 includes a base rail attachment 42 that allows a user to place the adjustable mount arm 18 on a bedside surgical rail 46. In some embodiment, the base rail attachment 42 includes a clamp 50 and a knob 54 for adjusting the clamp 50. For example, a user may loosen the knob 54; place the clamp 50 onto the bed rail 46; and tighten the knob 54 to secure the clamp 50 and the adjustable mount arm 18 to the bed rail 46.

With continued reference to FIG. 2, the adjustable mount arm 18 includes a first member 58 and a second member 62 rotatably coupled by an adjustable elbow 66. The adjustable elbow 66 includes a knob 70 to releasably lock the adjustable elbow 66 in a desired position. For example, a user may loosen the knob 70; articulate the adjustable elbow 66 to position the first and second members 58, 62 in the desired positions; and tighten the knob 70 to secure the adjustable elbow 66 and members 58, 62 in position.

With continued reference to FIG. 2, the adjustable mount arm 18 includes a bronchoscope claw 74 with a plurality of gripping fingers 78. The bronchoscope claw 74 is configured to receive and hold the bronchoscope 26 in position relative to the adjustable mount arm 18. For example, the bronchoscope claw 74 is opened by a user and positioned around the bronchoscope 26 (e.g., the bronchoscope handle) to easily dock the bronchoscope 26 on the adjustable mount arm 18. In some embodiments, the plurality of gripping fingers 78 includes a non-scratch coating to prevent damage to the bronchoscope 26.

In operation, the adjustable mount arm 18 is attached to the bed rail 46 and the bronchoscope 26 is clasped within the bronchoscope claw 74. Next, the relative positions of the first member 58 and the second member 62 may be adjusted by moving the adjustable elbow 66. As such, the bronchoscope 26 is supported in a variety of positions relative to the bed rail 46 by the adjustable mount arm 18. In some embodiments, the claw 74 is aligned with the patient's mouth to help prevent the creation of bends in the bronchoscope.

With reference to FIG. 3, in some embodiments, the adjustable mount arm 18 includes a support bracket 82 to hold a power distribution module (PDM) 86 for the flexible ablation probe 38 on the adjustable mount arm 18 in close proximity to the bronchoscope 26. In some embodiments, the power distribution module 86 is removably coupled to the support bracket 82 with a dovetail slot arrangement. In some embodiments, the support bracket 82 includes a magnet 90 to help retain the power distribution module 86 in position relative to the support bracket 82. In the illustrated embodiment, the power distribution module 86 includes a power cord 94 extending therefrom. The power distribution module 86 is configured to be electrically coupled to the flexible ablation probe 38. In some embodiments, the power distribution module 86 controls the microwave energy emitted from the flexible probe 38.

With continued reference to FIG. 3, the flexible ablation probe 38 includes a plug 98 that is electrically coupled to the power distribution module 86. In the illustrated embodiment, the plug 98 includes keyed features to ensure proper orientation of the plug 98 relative to the power distribution module 86. In some embodiments, the flexible probe 38 is then inserted directly into the bronchoscope 26 (FIG. 3). In the illustrated embodiment, the flexible probe 38 is inserted into a port 102 formed on the bronchoscope 102. In some embodiments, the flexible ablation probe 38 can provide therapy by delivering microwave energy to targeted tumors.

Figure 4:
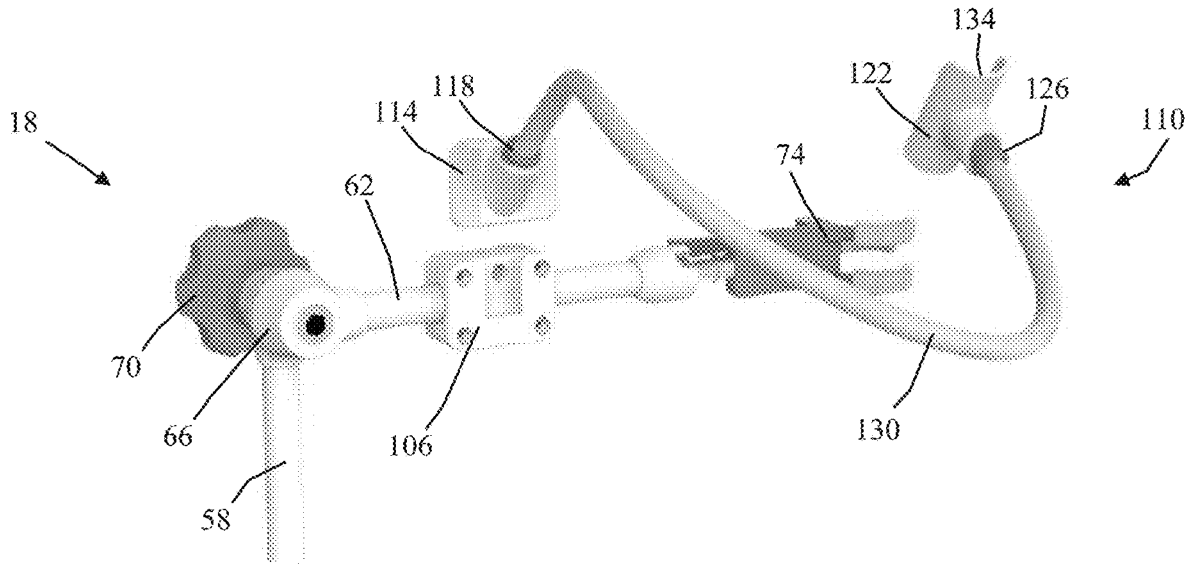
FIG. 4 is a partial perspective view of a gooseneck dock removably mounted to the adjustable mount arm of FIG. 2.

With reference to FIG. 4, in some embodiments, the adjustable mount arm 18 includes a support bracket 106 for a gooseneck dock 110. In the illustrated embodiment, the gooseneck dock 110 includes a mount 114 removably coupled to the support bracket 106 at a first end 118 and a cradle 122 for supporting a steerable sheath or other tool at a second end 126. In some embodiments, the cradle 122 is configured to support a variety of endoscopic tools or therapy devices. In some embodiments, the mount 114 is removably coupled to the support bracket 106 with a dovetail arrangement. In some embodiments, the dovetail arrangement is the same dovetail arrangement for mounting the power distribution module 86 to the support bracket 82.

A flexible member 130 extends between the mount 114 and the cradle 122, and the flexible member 130 is repositionable by a user, and the flexible member 130 retains its shape and position when released by a user. In other words, the flexible member 130 has sufficient strength to support a tool (e.g., a steerable sheath) in a variety of positions and orientations and can be manipulated with a single hand to move the cradle 122 and the tool to different locations.

Figure 5:
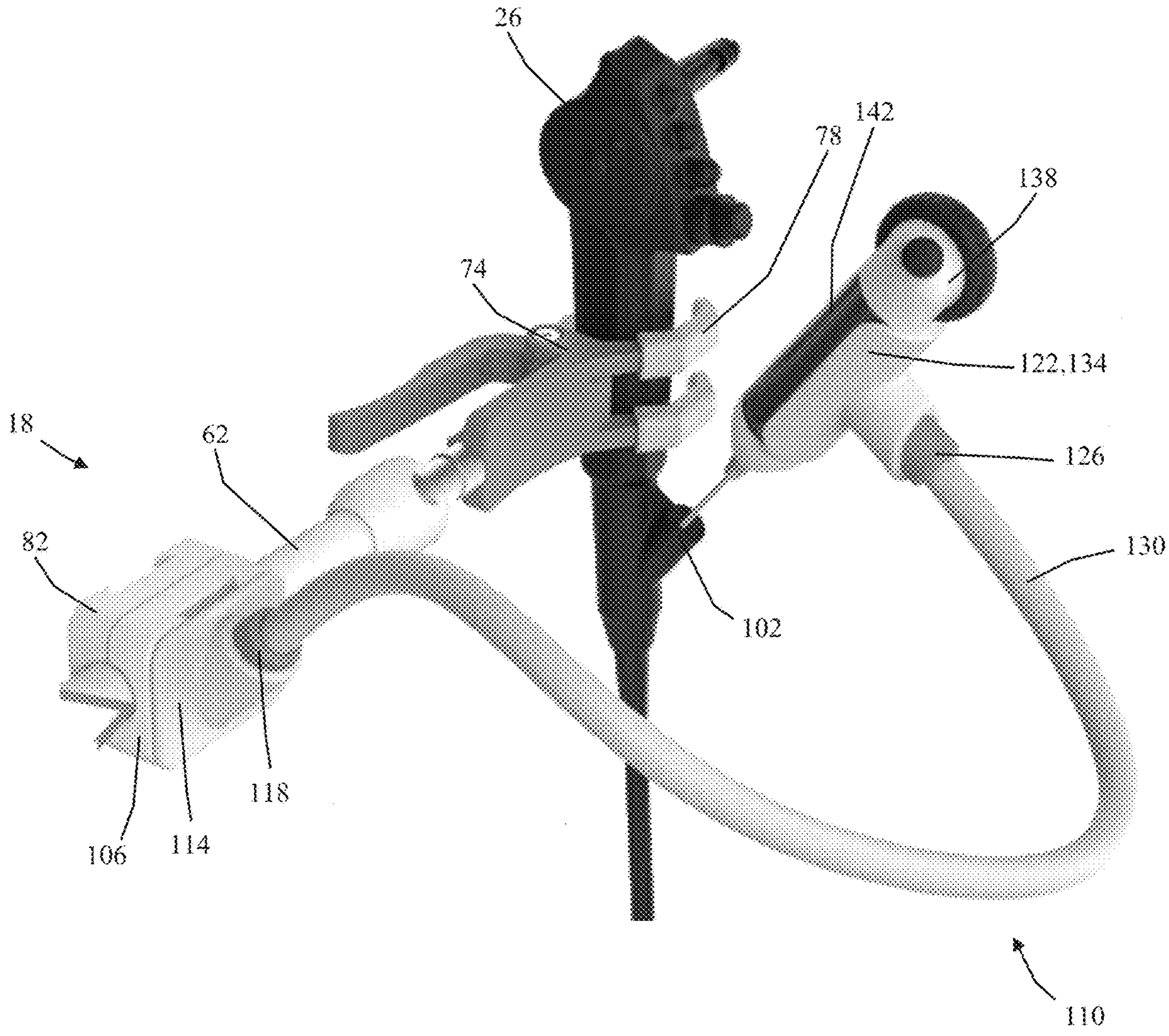
FIG. 5 is a partial perspective view of a system for use in an endoscopic procedure.

With reference to FIG. 5, the cradle 122 includes a magnetic mount 134 that magnetically couples to a steerable sheath 138. In the illustrated embodiment, the steerable sheath 138 includes a ferrous portion 142 (i.e., a ferrous sleeve) that is magnetically attracted to the magnetic mount 134. The magnetic mount 134 allows for the user to make finite position manipulations of the steerable sheath 138 (e.g., rotation, insertion, winnowing, etc.) while the steerable sheath 138 remains coupled to the cradle 122. The cradle 122 stabilizes the steerable sheath 138 for insertion of the steerable sheath 138 into the bronchoscope 26. Advantageously, the gooseneck dock 110 supports the steerable sheath 138 while the steerable sheath 138 is positioned within the bronchoscope 26. The gooseneck dock 110 is scope agnostic (i.e., can work with any type of endoscope) and can hold a tool in various positions and orientations with respect to a scope.

Figure 6:
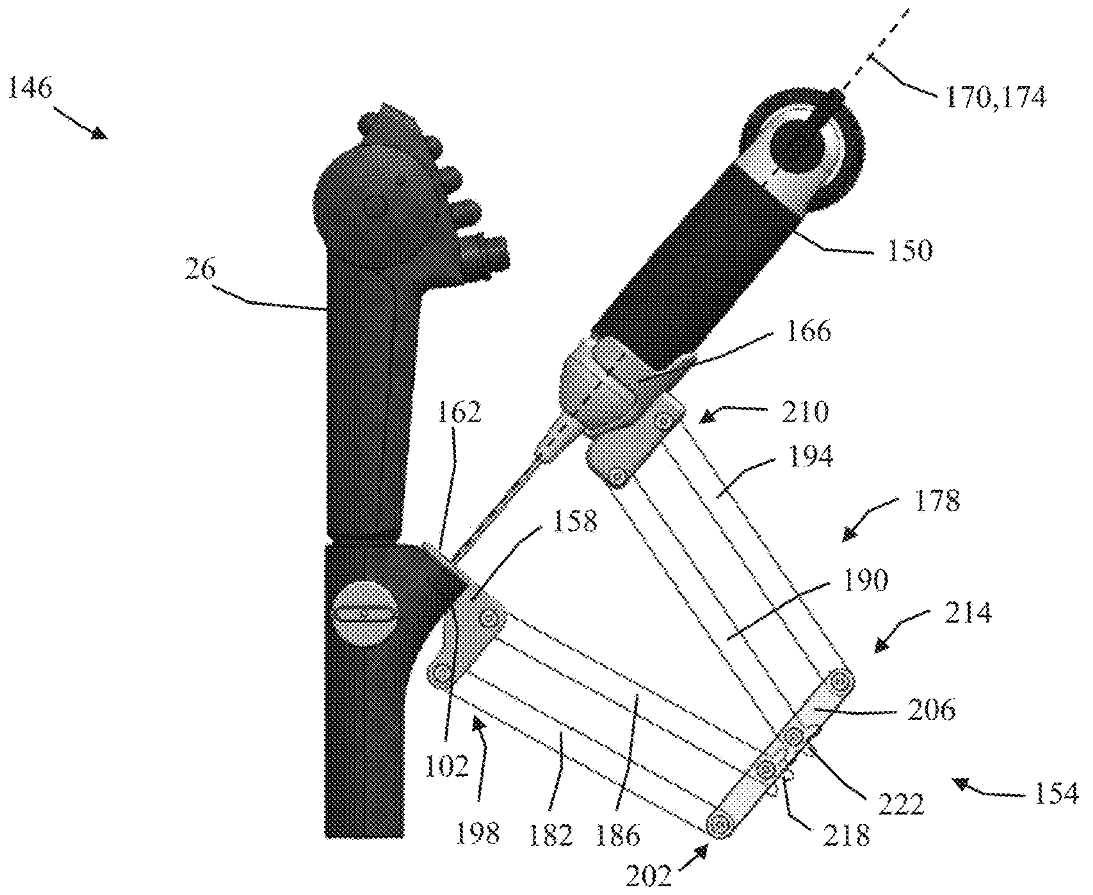
FIG. 6 is a side view of a bronchoscope attachment and a steerable sheath coupled to a bronchoscope.

With reference to FIG. 6, a system 146 is illustrated with the bronchoscope 26, a steerable sheath 150, and a bronchoscope attachment 154. In the illustrated embodiment, the bronchoscope attachment 154 includes a mount 158 with a port 162 (e.g., an aperture) corresponding to the port 102 on the bronchoscope 26. The bronchoscope attachment 154 further includes a cradle 166 that defines an insertion axis 170. In the illustrated embodiment, the insertion axis 170 of the cradle 166 is aligned with an insertion axis 174 of the port 102 on the bronchoscope 26.

With continued reference to FIG. 6, the bronchoscope attachment 154 includes a linkage 178 positioned between the mount 158 and the cradle 166. As explained in greater detail herein, the linkage 174 is movable between a first position in which the cradle 166 is positioned a first distance from the port 102 and the insertion axis 170 is aligned with the insertion axis 174 of the port 102, and a second position in which the cradle 166 is positioned a second distance from the port 102 and the insertion axis 170 is aligned with the insertion axis 174 of the port 102. In other words, the linkage 178 is movable to adjust the distance the cradle 166 is positioned from the port 102, while keeping the insertion axis 170 of the cradle 166 aligned with the port 102. As such, the insertion axis 170 remains aligned with the insertion axis 174 of the port 102 in response to movement of the linkage 178.

With continued reference to FIG. 6, the linkage 178 includes a first link 182, a second link 186, a third link 190, and a fourth link 194. At a first end 198, the first link 182 and the second link 186 are coupled to the mount 158. At a second end 202, opposite the first end 198, the first link 182 and the second link 186 are coupled to an elbow 206. At a first end 210, the third link 190 and the fourth link 194 are coupled to the cradle 166. At a second end 214, opposite the first end 210, the third link 190 and the fourth link 194 are coupled to the elbow 206. In the illustrated embodiment, the elbow 206 includes a first gear 218 coupled to the second link 186 and a second gear 222 coupled to the third link 190 such that the second and third links 186, 190 are rotatably coupled together. In the illustrated embodiment, the first gear 218 is integrally formed with the second link 186 and the second gear 222 is integrally formed with the third link 190. Advantageously, the third and fourth links 190, 194 move in response to movement of the first and second links 182, 186 (and vice versa) such that the distance between the cradle 166 and the bronchoscope 26 changes while maintaining the insertion axis 170 aligned with the port 102 on the bronchoscope 26.

Figure 7:
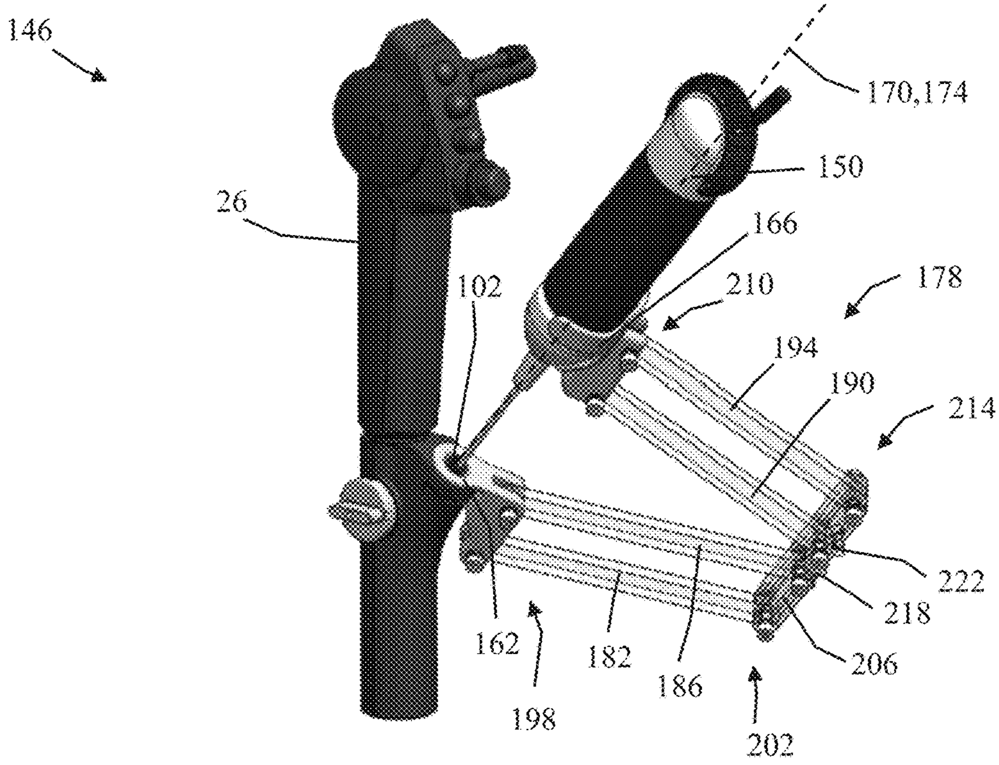
FIG. 7 is a perspective view of FIG. 6, with the bronchoscope attachment rotated with respect to the bronchoscope.

With reference to FIG. 7, in the illustrated embodiment, the mount 158 of the bronchoscope attachment 154 is rotatable with respect to the bronchoscope 26. In other words, the bronchoscope attachment 154 is rotatable about the insertion axis 170 and the insertion axis 174 extending through the ports 162, 102 respectively. The port 162 on the mount 158 remains in position as the mount 158 rotates about the port 162. Advantageously, the bronchoscope attachment 154 can be rotated about the insertion axis 170, 174 by a user during a procedure as desired.

Figure 8:
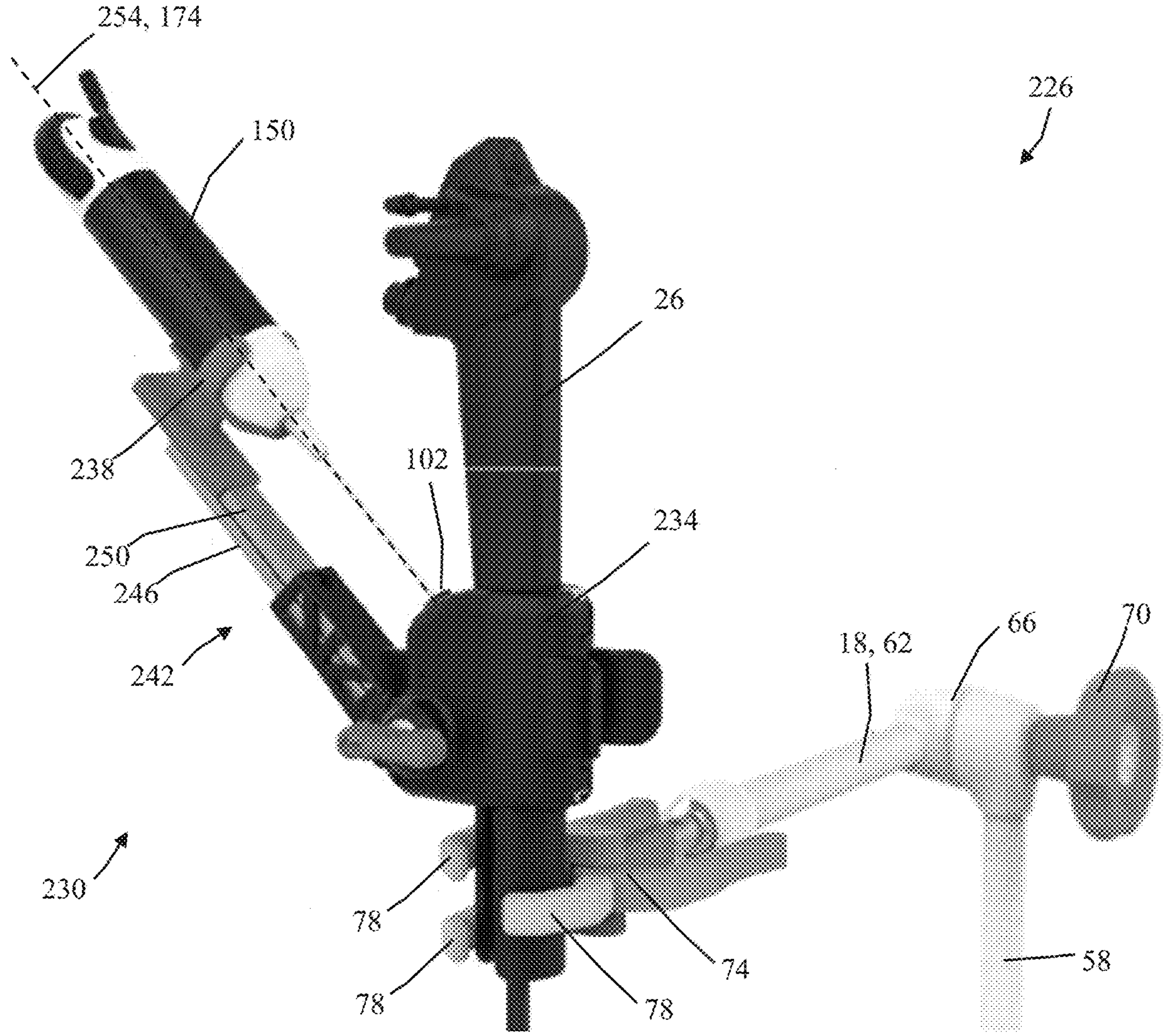
FIG. 8 is a partial perspective view of a system for use in an endoscopic procedure.

With reference to FIG. 8, a system 226 is illustrated with the adjustable mount arm 18, a bronchoscope attachment 230, the steerable sheath 150, and the bronchoscope 26. The bronchoscope attachment 230 includes a mount 234, a cradle 238, and a linkage 242 that is a telescopic slide extending between the mount 234 and the cradle 238. In the illustrated embodiment, the linkage 242 includes a first slide member 246 and a second slide member 250, and the slide members 246, 250 are slidable with respect to each other to position the cradle 238 a variety of distances from the bronchoscope 26 while maintain alignment of an insertion axis 254 of the cradle 238 with the insertion axis 174 of the bronchoscope port 102.

Figure 9:
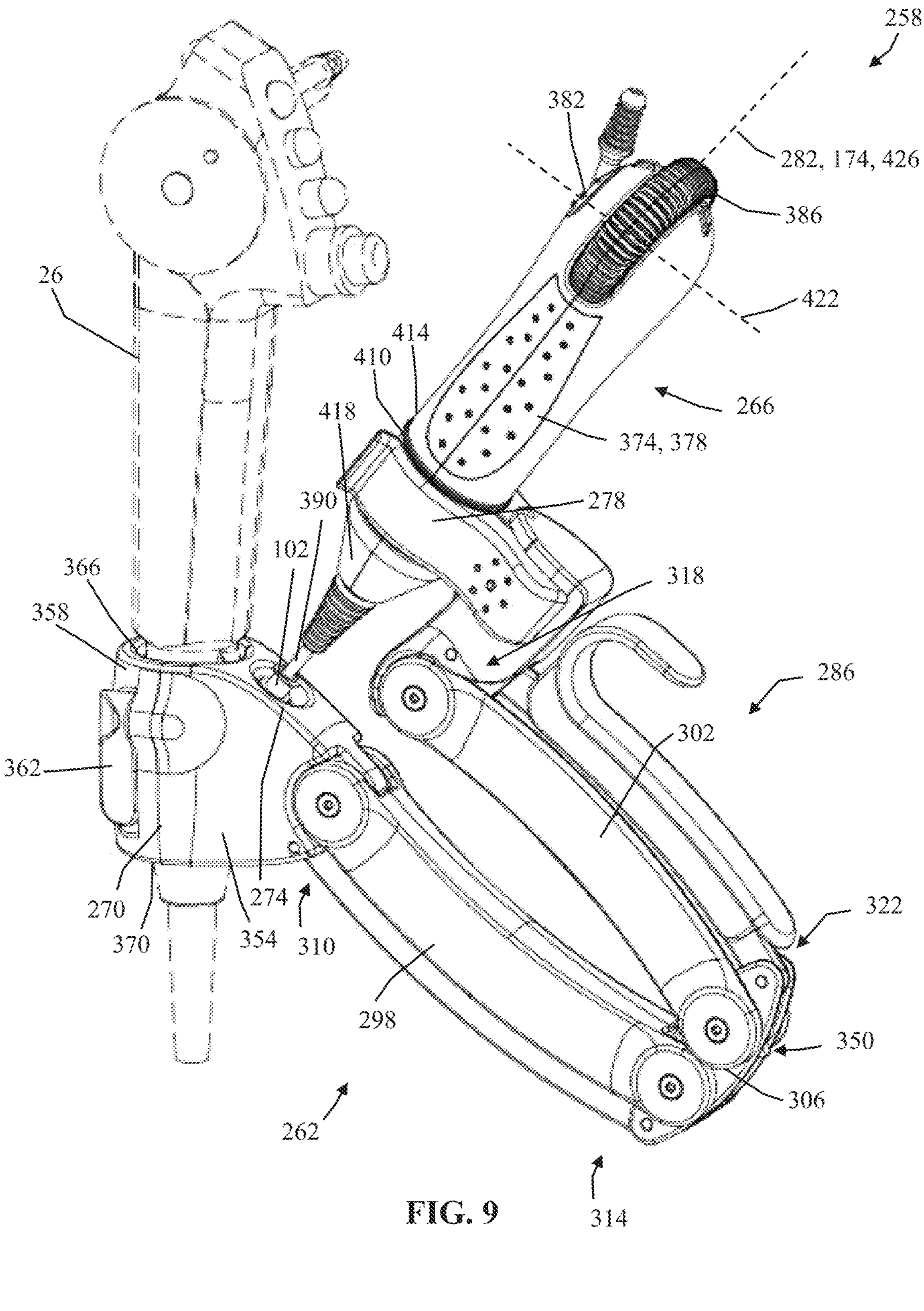
FIG. 9 is a perspective view of a bronchoscope attachment and a steerable sheath, with a bronchoscope shown in phantom lines.
Figure 13A:
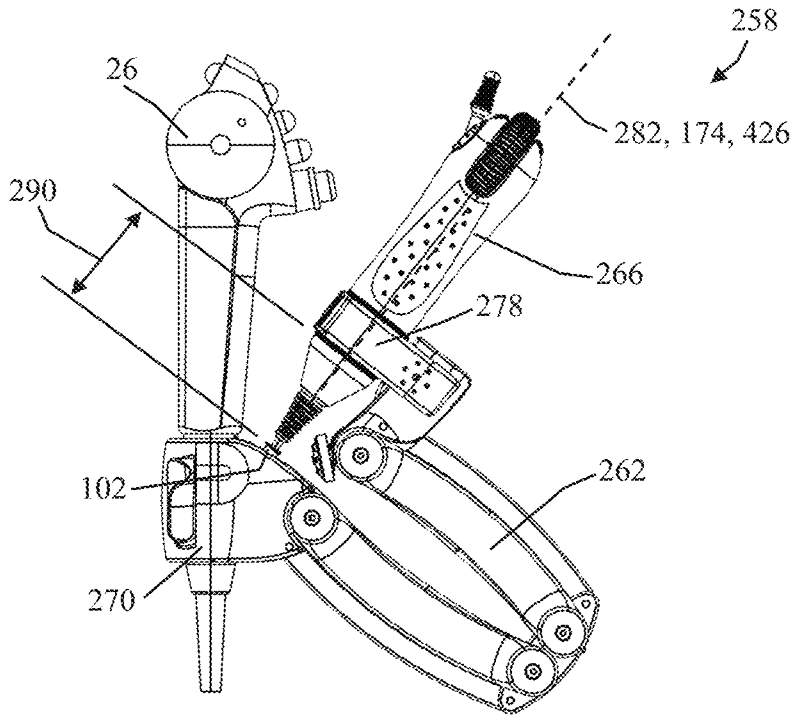
FIG. 13A is a side view of a system with a bronchoscope attachment and steerable sheath in a first position.
Figure 13B:
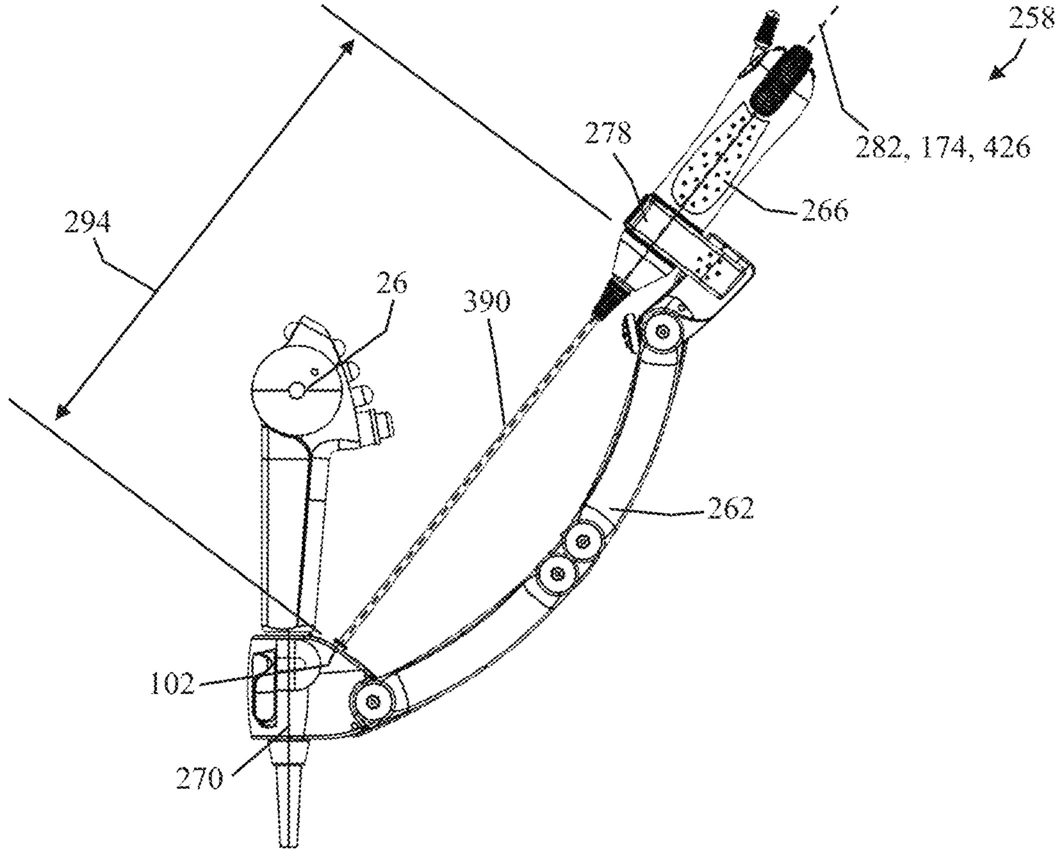
FIG. 13B is a side view of the system of FIG. 13A with the bronchoscope attachment and steerable sheath in a second position.

With reference to FIG. 9, a system 258 is illustrated with the bronchoscope 26, a bronchoscope attachment 262 (i.e., a support arm, a symmetric arm), and a steerable sheath 266. The bronchoscope attachment 262 includes a mount 270 with a port 274 corresponding to the port 102 on the bronchoscope 26. The bronchoscope attachment 262 further includes a cradle 278 defining an insertion axis 282 that is aligned with the insertion axis 174 of the port 102. A linkage 286 is positioned between the mount 270 and the cradle 278. The linkage 286 is movable between a first position (FIG. 13A) in which the cradle 278 is positioned a first distance 290 from the port 102 and the insertion axis 282 is aligned with the insertion axis 174 of the port 102; and a second position (FIG. 13B) in which the cradle 278 is positioned a second distance 294 from the port 102 and the insertion axis 282 is aligned with the insertion axis 174 of the port 102. In other words, the linkage 286 is movable to adjust the distance the cradle 278 is positioned from the port 102 on the bronchoscope 26 while keeping the insertion axis 282 aligned with the port 102. As such, the insertion axis 282 of the cradle 278 remains aligned with the insertion axis 174 of the port 102 in response to movement of the linkage 286.

Advantageously, the bronchoscope attachments disclosed herein (e.g., bronchoscope attachment 154, 230, 262) allows a single user to hold and manipulate both the bronchoscope and the steerable sheath as a single unit with a single hand. The bronchoscope attachment solves the problem of needing multiple operators to control a variety of devices during a medical procedure. The bronchoscope attachment can be attached to the bronchoscope with one hand. The bronchoscope attachment maintains the position and distance of the sheath relative to the bronchoscope working channel port. The cradle provides a snap-fit design to easily click in and out the steerable sheath. The bronchoscope attachment also reduces the likelihood of the sheath kinking because the insertion axes remain aligned. In some embodiments, the bronchoscope attachment is configured to support a variety of endoscopic tools or therapy devices. In some embodiments, the bronchoscope attachment is coupled to the adjustable mount arm 18.

Figure 10:
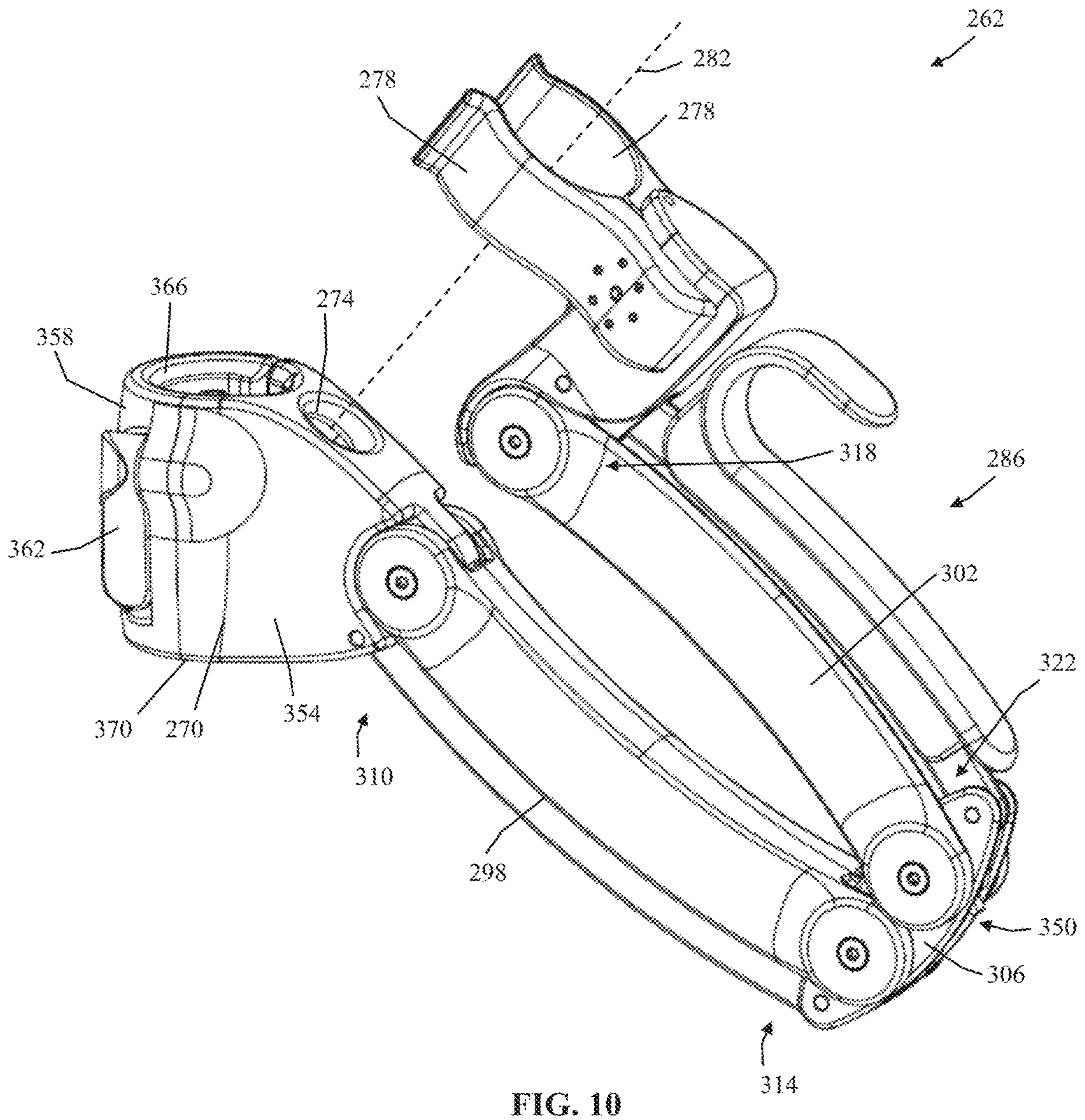
FIG. 10 is a perspective view of the bronchoscope attachment of FIG. 9.
Figure 12:
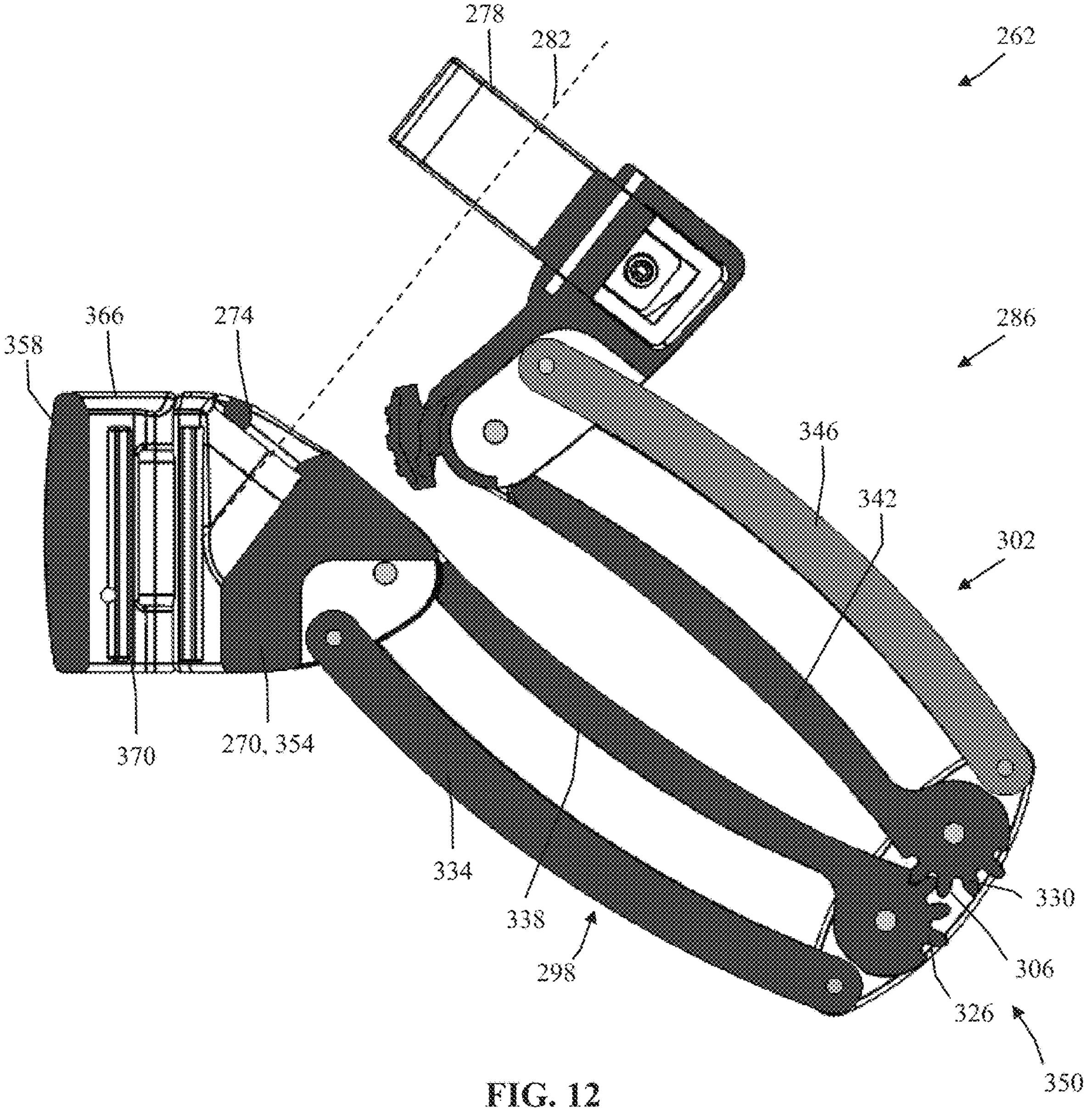
FIG. 12 is a cross-sectional view of the bronchoscope attachment of FIG. 9.

With reference to FIGS. 10 and 12, the linkage 286 includes a first arm 298, a second end 302, and an elbow 306 coupled between the first arm 298 and the second arm 302. A first end 310 of the first arm 298 is pivotably coupled to the mount 270, and a second end 314 of the first arm 298 is pivotably coupled to the elbow 306. A first end 318 of the second arm 302 is coupled to the cradle 278, and a second end 322 of the second arm 302 is pivotably coupled to the elbow 306. In the illustrated embodiment, the elbow 306 includes a first gear 326 coupled to the first arm 298 and a second gear 330 coupled to the second arm 302. In the illustrated embodiment, the first gear 326 is enmeshed with the second gear 330.

With continued reference to FIG. 12, the first arm 298 includes a first link 334 and a second link 338, and the second arm 302 includes a third link 342 and a fourth link 346. In the illustrated embodiment, the second link 338 and the third link 342 are rotatably coupled together by a gear set 350 (i.e., the first gear 326 and the second gear 330) positioned in the elbow 306. In the illustrated embodiment, the first gear 326 is integrally formed with the second link 338 and the second gear 330 is integrally formed with the third link 342. As such, the second arm 302 moves in response to movement of the first arm 298, and the first arm 298 moves in response to movement of the second arm 302. The linkage 286 permits smooth insertion and retraction of the steerable sheath 266 while maintaining the same insertion trajectory along the insertion axis 174 (i.e., the insertion axis 282 remains aligned with the insertion axis 174). For example, an operator can pull on the second arm 302 or cradle 278 to retract the steerable sheath 266 from the bronchoscope 26 or push down on the second arm 302 or cradle 278 to insert the steerable sheath 266 into the bronchoscope 26, while maintain alignment of axes 282, 174).

Figure 11A:
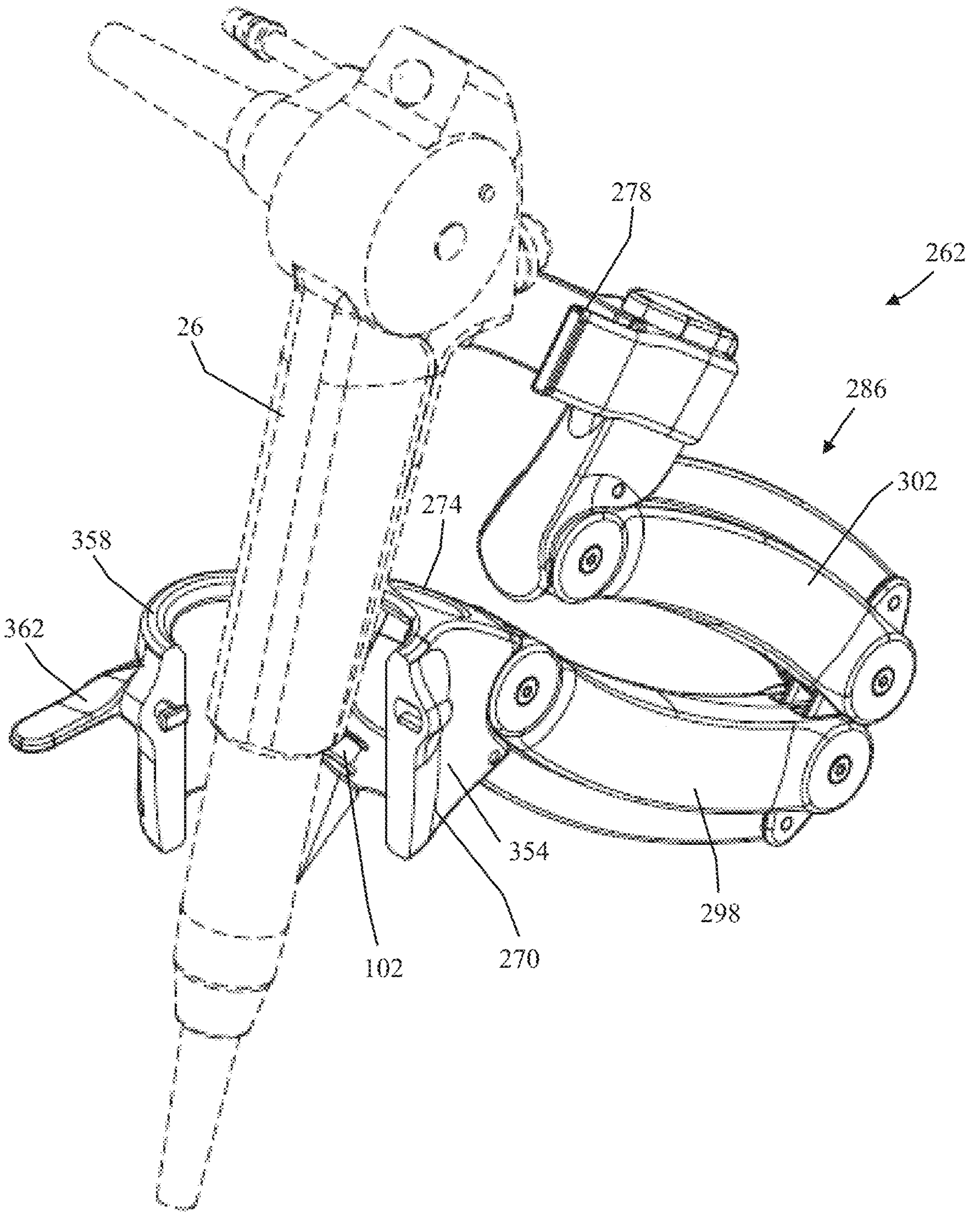
FIG. 11A is a perspective view of the bronchoscope attachment of FIG. 9, separated from the bronchoscope.
Figure 11B:
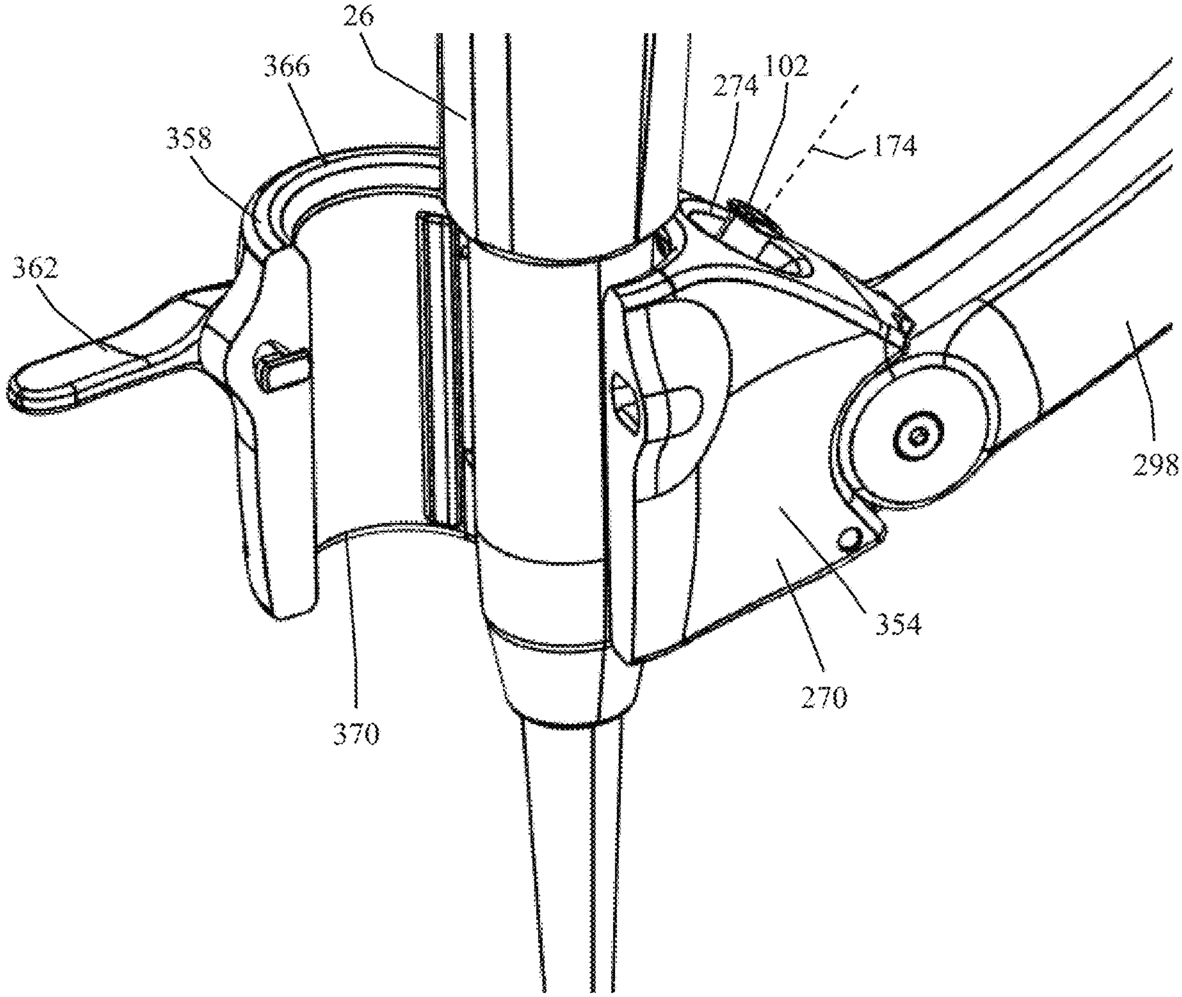
FIG. 11B is partial perspective view of the bronchoscope attachment of FIG. 9, supported on a bronchoscope in a partially installed configuration.

With reference to FIGS. 10, 11A, and 11B, the mount 270 is a collar with a base portion 354 and a door 358 movable with respect to the base portion 354 between an open position (FIGS. 11A and 11B) and a closed position (FIGS. 9 and 10). The mount 270 further includes a latch 362 to selectively lock the door 358 in the closed position. In the illustrated embodiment, the latch 362 is actuated by a user to lock the door 358 in the closed position. In some embodiments, the mount 270 at least partially wraps around the bronchoscope 26. In the illustrated embodiment, the base portion 354 and the door 358 together wrap entirely around the bronchoscope 26 when the door 358 is in the closed position. The mount 270 includes a first opening 366 partially defined by the door 358 and a second opening 370 at least partially defined by the door 358. In the illustrated embodiment, the first opening 366 is aligned with the second opening 370 and both openings 366, 370 are configured to receive the bronchoscope 26 such that the bronchoscope 26 extends through both the first opening 366 and the second opening 370.

With reference to FIGS. 9 and 10, the port 274 of the mount 270 is formed in the base portion 354. In the illustrated embodiment, the port 274 is an aperture configured to receive the port 102 of the bronchoscope 26. In other words, the port 102 on the bronchoscope 26 extends through the port 274 of the mount 270. In some embodiments, a seal is coupled to the port 274 and or the port 102 to create a seal around any tool or instrument inserted into the bronchoscope 26. In other words, the seal creates an airtight seal around devices inserted into the bronchoscope 26 and allows operators to immediately act in response to emergencies without requiring disassembly of the bronchoscope attachment 262.

Advantageously, the bronchoscope attachment 262 is configured to rest (i.e., to be supported by, hung from, etc.) the bronchoscope 26 during installation of the bronchoscope attachment 262. In other words, after the mount 270 is coupled to the bronchoscope 26 such that the port 102 extends through the port 274, the bronchoscope attachment 262 is supported on the bronchoscope 26 such that an operator could remove their hands from the bronchoscope attachment 262 and the bronchoscope attachment 262 remains in position. As such, the bronchoscope attachment 262 is partially installed on the bronchoscope 26 with the door 358 in the open position (moving from FIGS. 11A to FIG. 11B), and then the bronchoscope attachment 262 is fully supported on the bronchoscope 26. Advantageously, the bronchoscope attachment 262 is more easily attached to the bronchoscope 26 with fewer operator hands required. For example, the operator is able to install (or partially install) the bronchoscope attachment 262 onto the bronchoscope 26 with one hand before or after navigation of the bronchoscope 26. The door 358 is then moved to the closed position, and the latch 362 is actuated to secure the door 358 in the closed position to secure the bronchoscope attachment 262 to the bronchoscope 26. To remove the bronchoscope attachment 262 from the bronchoscope 26, the latch 362 is actuated to release the door 358 and allow the door 358 to move from the closed position to the open position. The base portion 354, the linkage 286, and the cradle 278 remain in position in response to the door 358 moving from the closed position to the open position. In other words, the bronchoscope attachment 262 remains supported on the bronchoscope 26 when the door 358 is moved to the open position.

Figure 14:
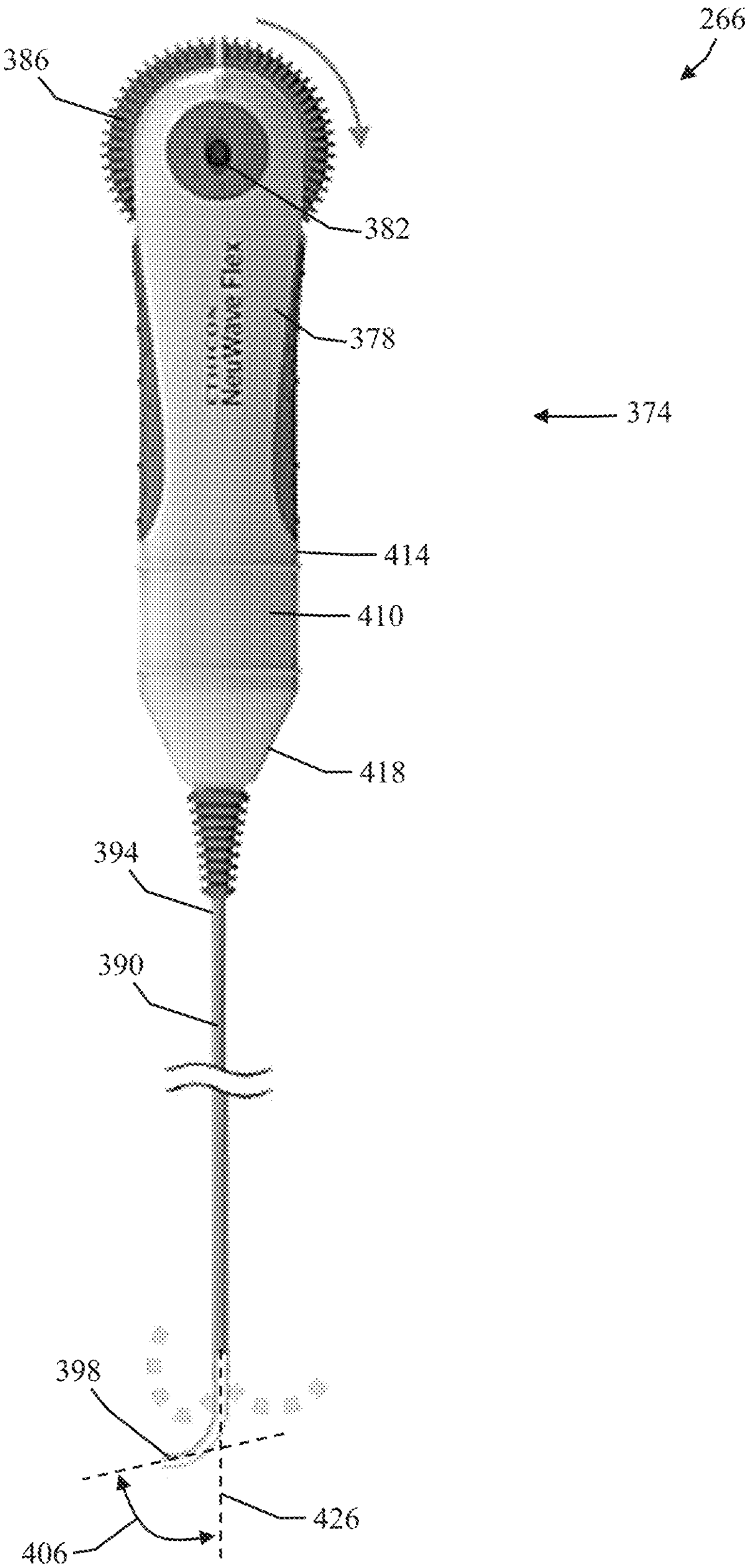
FIG. 14 is a side view of a steerable sheath.

With reference to FIG. 14, the steerable sheath 266 includes a handle 374 with a housing 378, a port 382 formed on the housing 378, and a user input wheel 386 rotatably coupled to the housing 378. A sheath 390 extends from the housing 378, and the sheath 390 includes a proximal end 394 coupled to the handle 374 and a distal end 398 opposite the proximal end 394. The distal end 398 is articulated by user actuation of the user input wheel 386, with two articulated positions shown in phantom lines in FIG. 14. A transmission 402 is coupled between the user input wheel 386 and the distal end 398 of the sheath 390, and actuation of the user input wheel 386 articulates the distal end 398 of the sheath 390. In the illustrated embodiment, the sheath 390 is a pre-curved sheath such that the distal end 398 is curved at an angle 406 while the user input wheel 386 is in a neutral position. In some embodiments, the angle 406 is within a range of approximately 45 degrees to approximately 180 degrees. In some embodiments, the angle 406 is approximately 70 degrees. In some embodiment, the pre-curve allows for airway navigation without having to initially articulate. In some embodiments, articulation of the distal end with the pre-curve (i.e., articulation in the same direction of the pre-curve) allows for a greater amount or articulation in the direction of the pre-curve.

Figure 15:
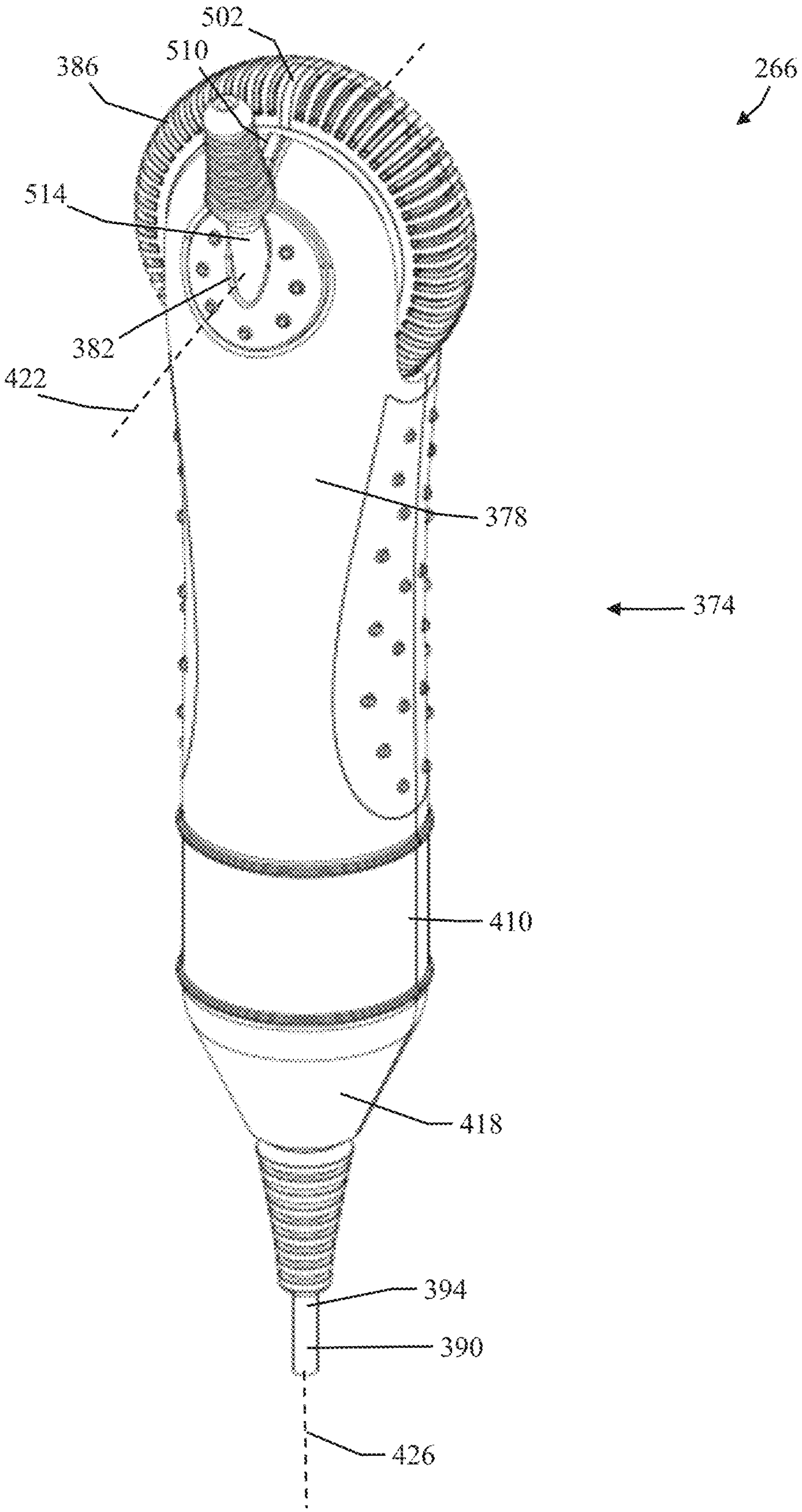
FIG. 15 is a partial perspective view of the steerable sheath of FIG. 14.

With reference to FIGS. 9 and 15, the handle 374 of the steerable sheath 266 snaps into the cradle 278. In other words, the steerable sheath 266 is releasably coupled to the cradle 278. In the illustrated embodiment, the handle 374 includes a circumferential groove 410 on an external surface 414 of the housing 378. In the illustrated embodiment, the circumferential groove 410 extends 360 degrees around the external surface 414 of the housing 378. In other embodiments, the circumferential groove 410 extends less than 360 degrees around the housing 378. The housing 378 includes a tapered end 418, and the proximal end 394 of the sheath 390 is coupled to the tapered end 418. As such, the cradle 278 is configured to hold the steerable sheath 266 in position during navigation, imaging, confirmation, and ablation. The sheath 390 can be rotated, articulated, inserted into the bronchoscope 26, and retracted from the bronchoscope 26 all while remaining docked in the cradle 278.

The precise positioning of the flexible probe 38 when used for lung ablation, for example, is challenging with conventional sheaths and extended working channels, which are primarily static with pre-curved ends that straighten during probe or tool insertion. Conventional sheaths to not provide means to change the trajectory of the probe once placed through the sheath and therefore can become dependent on the patient's airway structure to access the target lesion. Advantageously, the steerable sheaths disclosed herein (e.g., steerable sheath 34, 138, 150, 266, 434, 458, 482, 582, 642, 690) improve the precision and control over the positioning of the flexible probe 38. The steerable sheath can steer via articulation pull wires and can work with or without a bronchoscope. The steerable sheath allows one-hand use to control insertion and/or removable, rotation, and articulation in more than one direction. The steerable sheath facilitates use in a vertical position for a pulmonary procedure, in contrast to horizontal for sheaths used in cardiac procedures. In some embodiments, the steerable sheath may include axial symmetry to allow for the steerable sheath to be docked in a cradle and still rotate relative to the cradle. The steerable sheath does not require a robotic platform, which can be cost prohibitive. In some embodiments, the steerable sheath is utilized to place other endoscopic tools, therapy device, biopsy device, or local drug delivery device. In some embodiments, the system includes a local drug delivery device (e.g., a flexible needle) configured to be inserted through the steerable sheath and the bronchoscope. In some embodiments, the system includes a diagnostic biopsy tool configured to be inserted through the steerable sheath and the bronchoscope.

With reference to FIG. 15, the user input wheel 386 is rotatable about an axis 422 that intersects a sheath axis 426 defined by the sheath 390. In the illustrated embodiment, the axis 422 is perpendicular to the sheath axis 426. In the illustrated embodiment, the sheath axis 426 is also a longitudinal axis of the handle 374.

Figure 17:
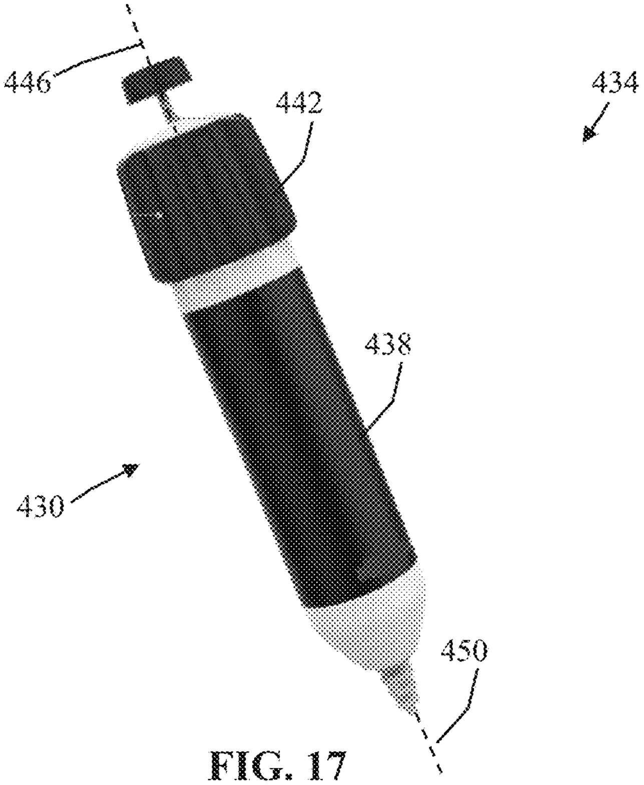
FIG. 17 is a perspective view of a steerable sheath.

With reference to FIG. 17, a handle 430 for a steerable sheath 434 is illustrated. The handle 430 includes a housing 438 and a user input wheel 442 that is rotatably coupled to the housing 438 about an axis 446 aligned with a longitudinal axis 450 of the handle 430 (which is also a sheath axis in the illustrate embodiment). In the illustrated embodiment, the user input wheel 442 is an actuator ring that wraps 360 degrees around an outer circumference 454 of the housing 438.

Figure 18:
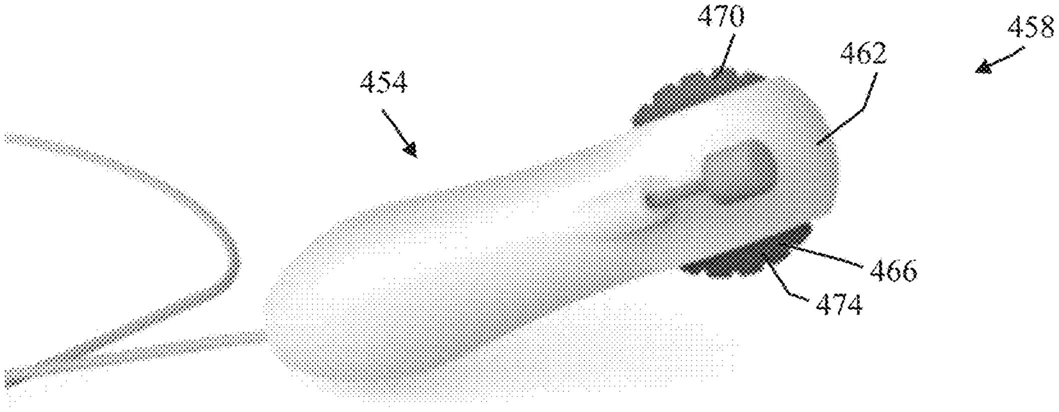
FIG. 18 is a perspective view of a steerable sheath.

With reference to FIG. 18, a handle 454 for a steerable sheath 458 is illustrated. The handle 454 includes a housing 462 and a user input wheel 466 that is positioned within the housing 462 with a first exposed portion 470 and a second exposed portion 474. The housing 462 is positioned between the first exposed portion 470 and the second exposed portion 474. In other words, the user input wheel 466 extends from the housing 462 at two distinct locations with a portion of the housing 462 separated the two portions 470, 474.

Figure 19:
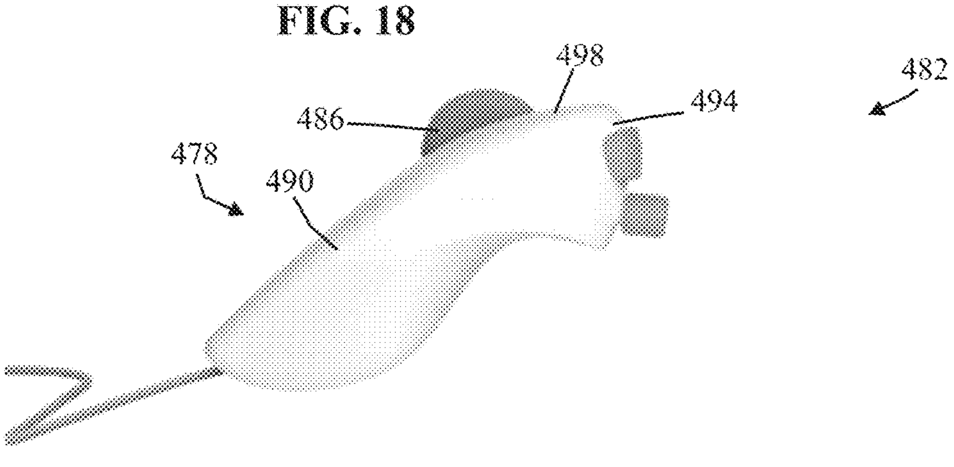
FIG. 19 is a perspective view of a steerable sheath.

With reference to FIG. 19, a handle 478 for a steerable sheath 482 is illustrated. The handle 478 includes a user input wheel 486 that is rotatably coupled to a housing 490. In the illustrated embodiment, the user input wheel 486 is spaced from a proximal end 494 of the housing 490 and extends from a top surface 498 of the housing 490.

Figure 16A:
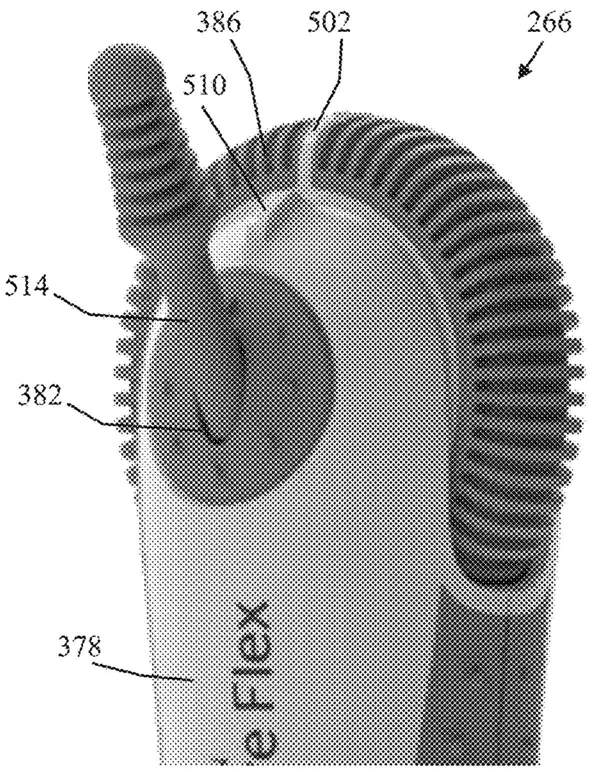
FIG. 16A is a partial perspective view of a steerable sheath with a user input wheel in a neutral position.
Figure 16B:
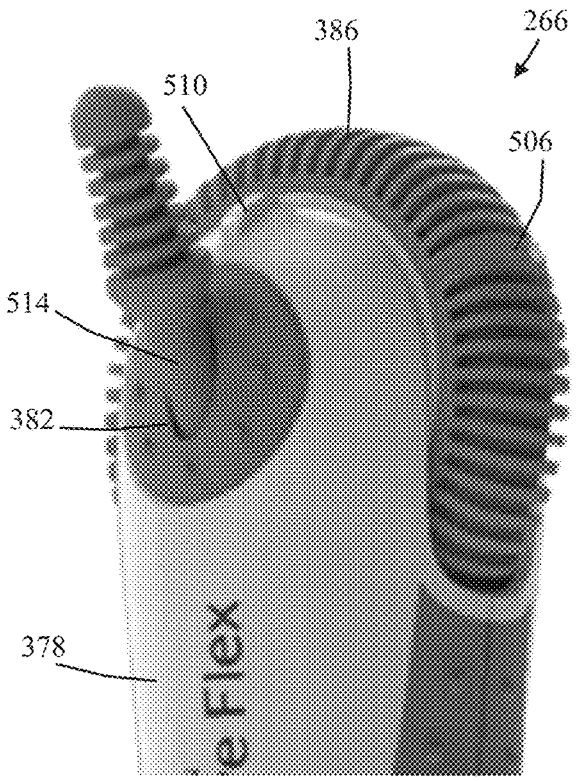
FIG. 16B is a partial perspective view of a steerable sheath with a user input wheel in an actuated position.
Figure 16C:
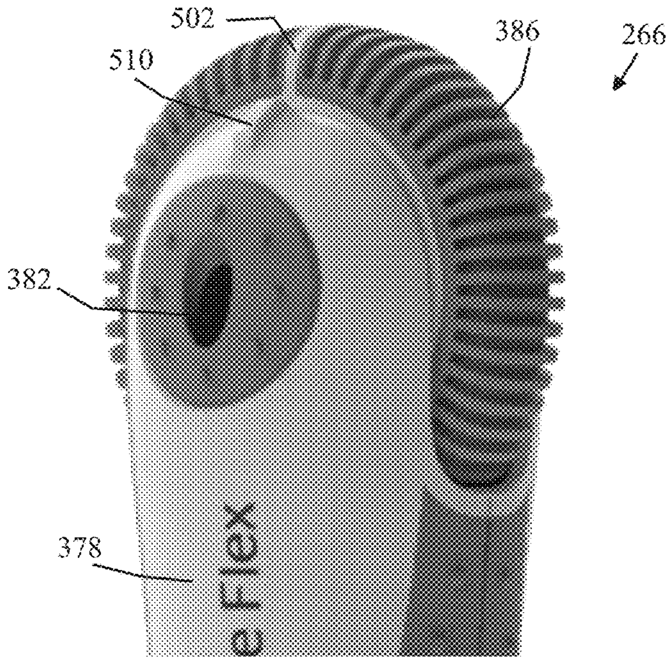
FIG. 16C is a partial perspective view of a steerable sheath with an obturator removed from a port.

With reference to FIGS. 16A-16C, the user input wheel 386 of the steerable sheath 266 includes a first indicator 502 visible when the user input wheel 386 is in the neutral position (FIG. 16A) and a second indicator 506 visible when the user input wheel 386 is in a non-neutral position (FIG. 16B). In other words, the first indicator 502 provides indication to the operator that that distal end 398 of the sheath 390 is in the neural position. In the illustrated embodiment, the first indicator 502 aligns with a corresponding rib 510 formed on the housing 378 when the distal end 398 of the sheath 390 is in the neutral position. As detailed herein, in some embodiments, the distal end 398 of the sheath 390 is curved in the neutral position. The second indicator 506 provides indication to the operator that the distal end 398 of the sheath 390 is in an actuated position. In the illustrated embodiment, the second indicator 506 is a contrasting color (e.g., red) to alert the operator that the distal end 398 is actuated before, for example, the operator attempts to withdraw or retract the steerable sheath 266 partly or wholly from the bronchoscope 26. For example, prior to performing an ablation, the sheath distal end should be retracted out of the planned ablation zone.

Figure 23:
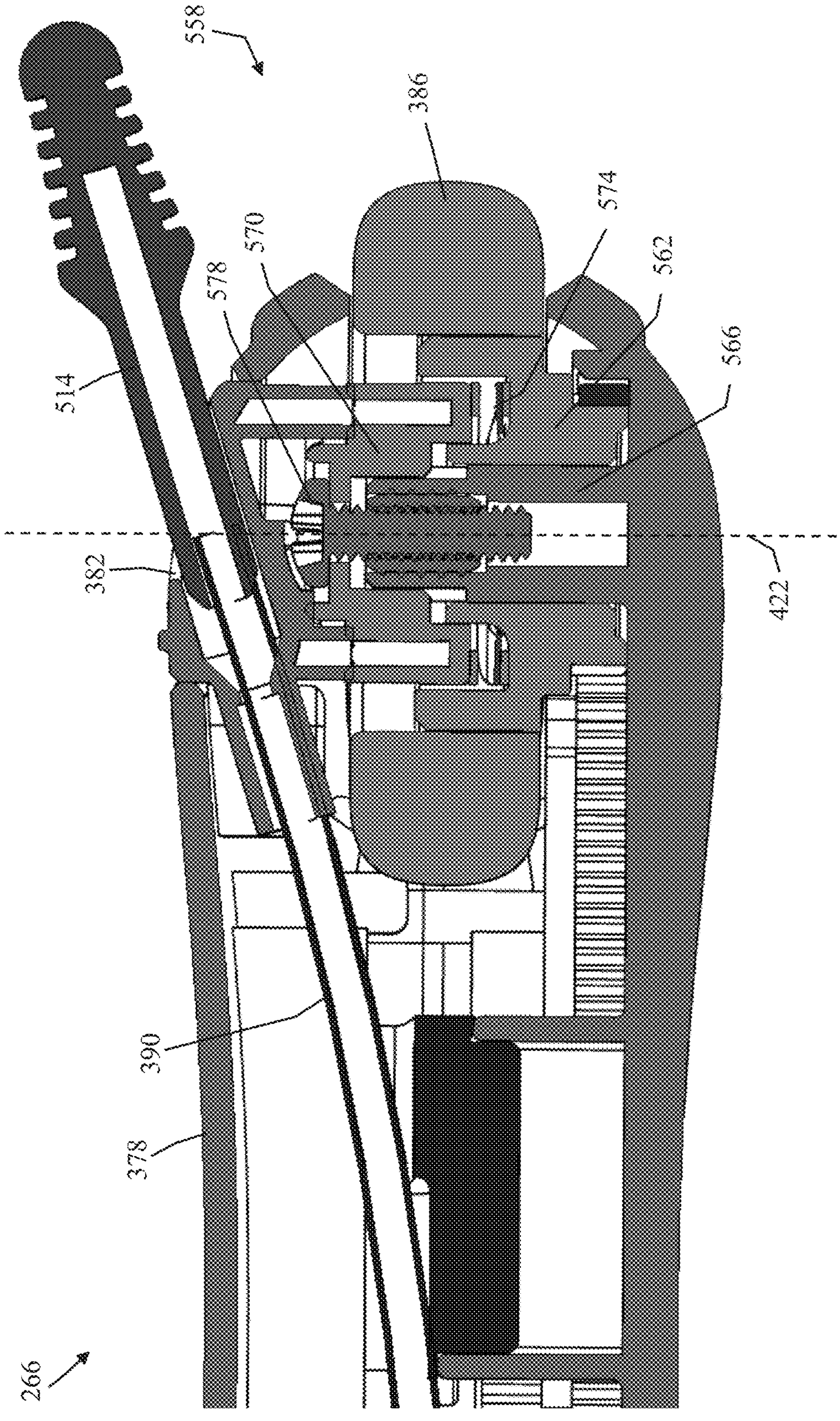
FIG. 23 is a partial cross-sectional view of the steerable sheath of FIG. 14.

An obturator 514 is insertable through the port 382 on the handle 374 and into the sheath 390 to aid in positioning of the sheath 390 in the bronchoscope 26, for example. With reference to FIG. 23, the port 382 is connected to the sheath 390. In some embodiments, a friction fit holds the obturator 514 in place. The obturator 514 is removable from the port 382 (FIG. 16C). With obturator 514 removed, the port 382 is configured to receive the flexible probe 38. In some embodiments, the port 382 is funnel shaped.

Figure 20:
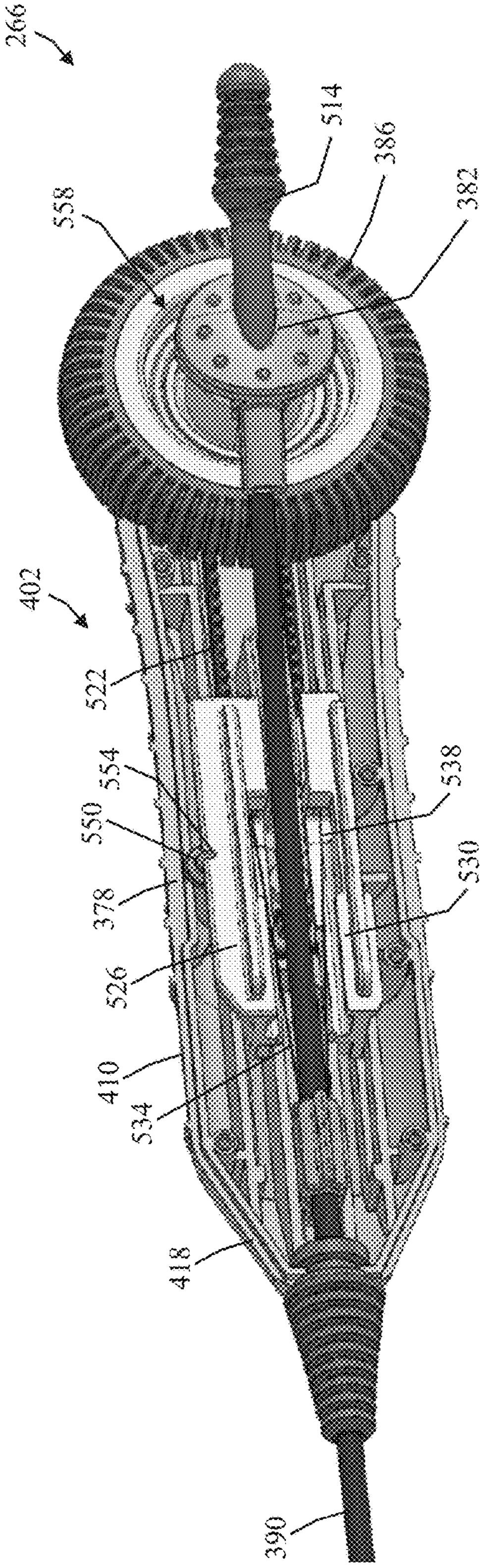
FIG. 20 is a partial side view of the steerable sheath of FIG. 14, with portions removed for clarity.
Figure 21:
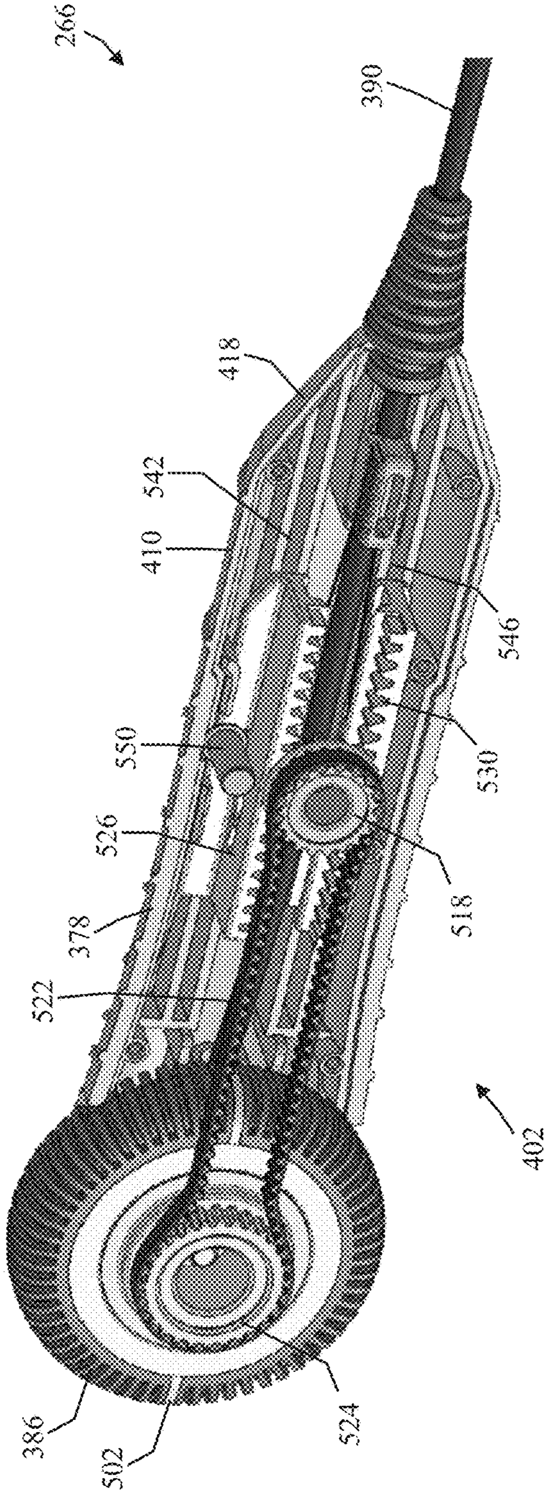
FIG. 21 is another partial side view of the steerable sheath of FIG. 14, with portions removed for clarity.
Figure 22:
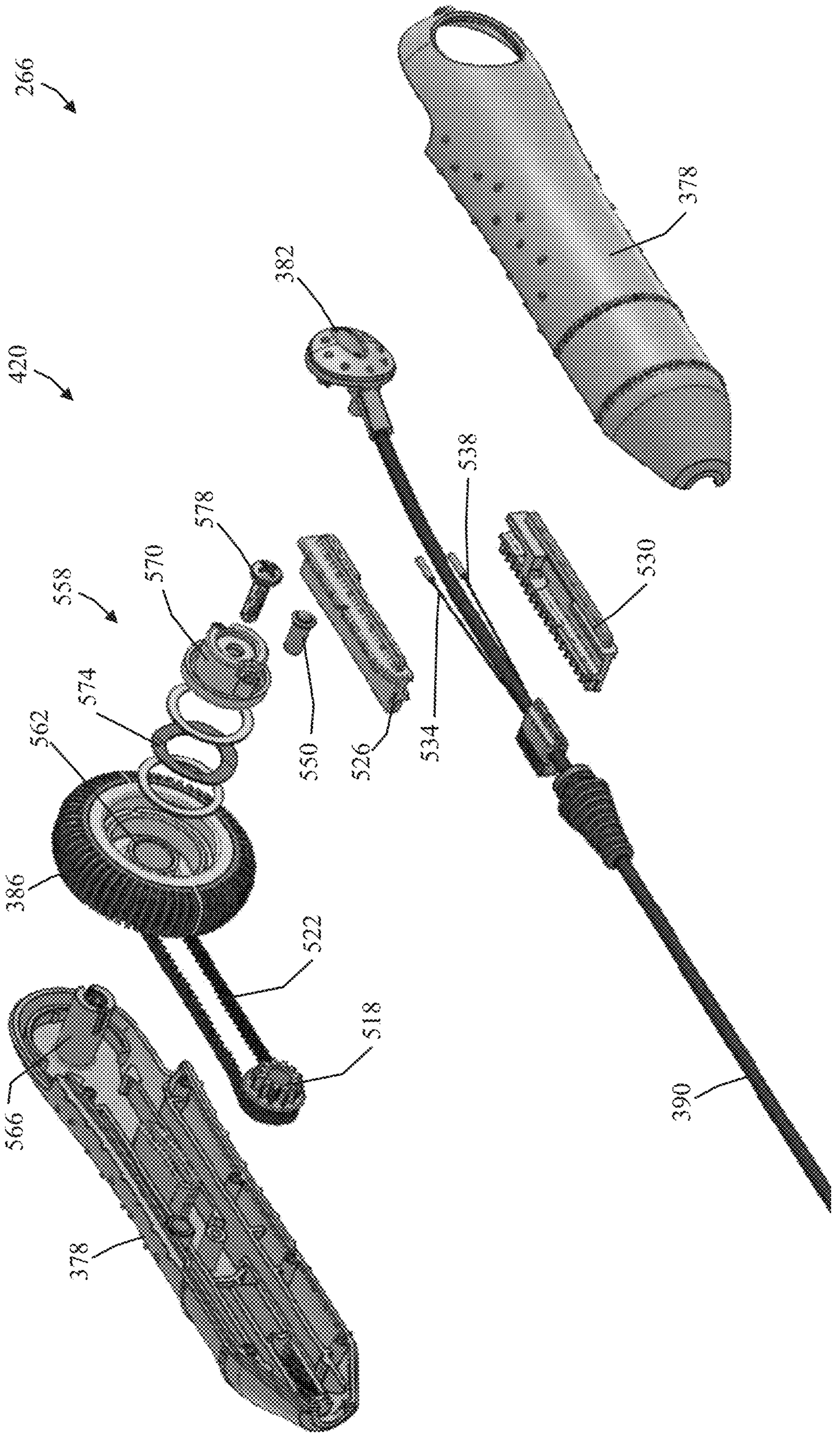
FIG. 22 is an exploded view of the steerable sheath of FIG. 14.

With reference to FIGS. 20-22, the transmission 402 of the steerable sheath 266 includes a drive gear 518 and a belt 522 coupled between the user input wheel 386 and the drive gear 518. In some embodiments, the belt 522 is a Kevlar belt. In the illustrated embodiment, the user input wheel 386 includes a gear 524 formed thereon and is coupled to the belt 522. In other words, the belt 522 rotatably couples the gear 524 with the drive gear 518. The transmission 402 further includes a first rack 526 enmeshed with the drive gear 518 and a second rack 530 enmeshed with the drive gear 518. A first pull wire 534 is coupled to the first rack 526 and a second pull wire 538 is coupled to the second rack 530. In some embodiments, the transmission includes only a single pull wire. In operation, the first rack 526 and the second rack 530 translate relative to the drive gear 518 in response to rotation of the drive gear 518 driven by the user input wheel 386. Translation of the first rack 526 and the second rack 530 relative to the housing 378 causes actuation of the first pull wire 534 and the second pull wire 538, which articulates the distal end 398 of the sheath 390. In some embodiments, actuation of the first pull wire 534 or the second pull wire 538 articulates the distal end 398 of the sheath 390. In some embodiments, the pull wires 534, 538 are attached on opposites sides of the distal end 398.

Figure 24:
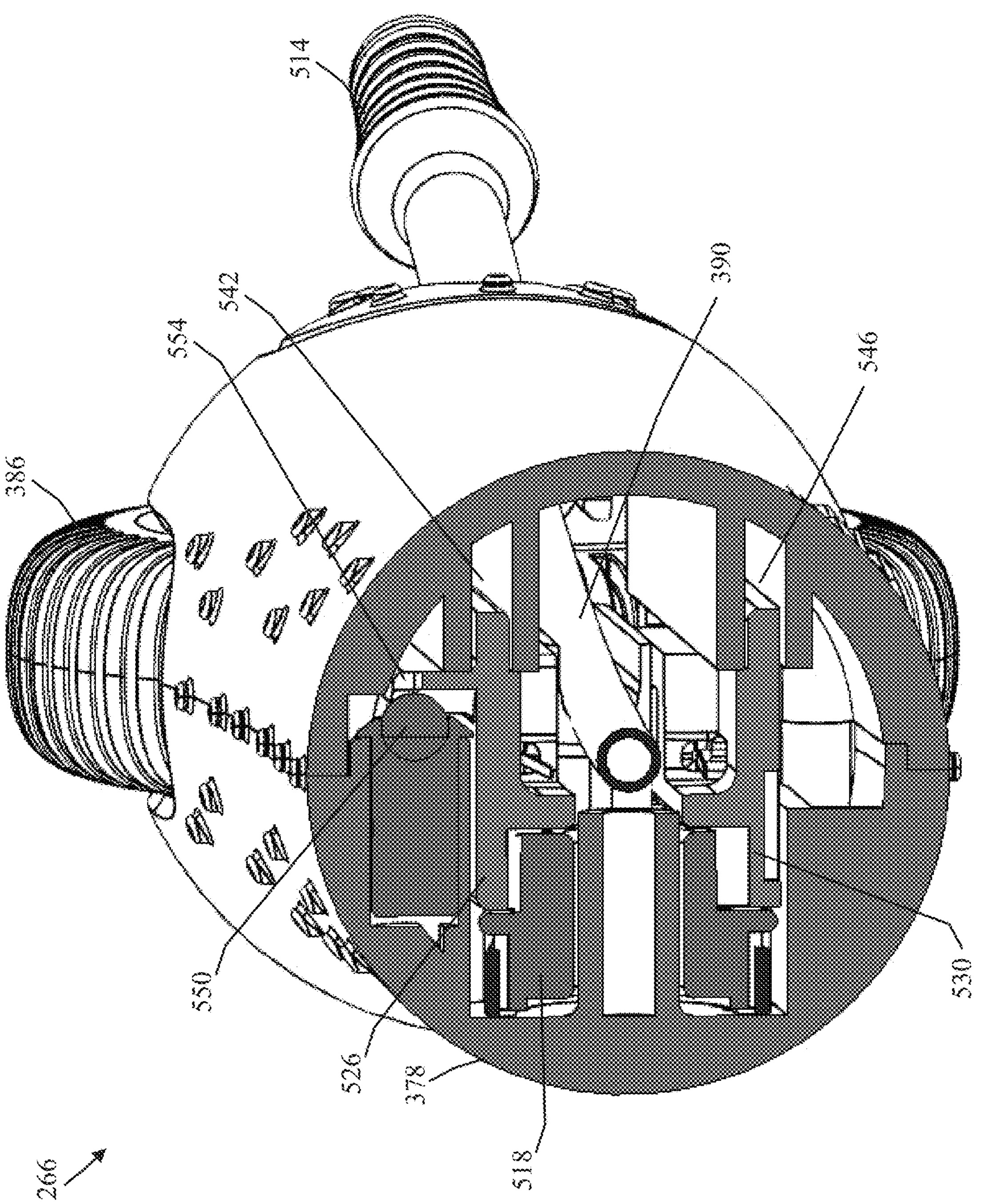
FIG. 24 is a perspective cross-sectional view of the steerable sheath of FIG. 14.

With reference to FIG. 24, the housing 378 includes a first slot 542 that at least partially receives the first rack 526 and a second slot 546 that at least partially receives the second rack 530. In the illustrated embodiment, the first rack 526 and the second rack 530 are slidable with respect to the housing 378 along the axis 426. A detent 550 is positioned within the housing 378, and the detent 550 engages the transmission 402 when the user input wheel 386 is in the neutral position (FIG. 24). In the illustrated embodiment, the detent 550 is a ball-spring detent that is at least partially received within a corresponding notch 554 formed in the first rack 526. As such, the detent 550 allows an operator to easily find and the neutral position for the user input wheel 386.

With reference to FIGS. 22 and 23, the steerable sheath 266 includes a braking assembly 558 that adjusts the amount of frictional engagement between the housing 378 and the user input wheel 386. In other words, the braking assembly 558 is configured to adjust the frictional resistance to rotating the user input wheel 386 about the axis 422. As detailed herein, the braking assembly 558 holds the position of the user input wheel 386 when the user input wheel 386 is released by a user. In other words, friction provided by the braking assembly 558 causes the user input wheel 386 to remain in the rotational positional left by the operator.

In the illustrated embodiment, the user input wheel 386 includes a hub 562 positioned around a boss 566 formed on the housing 378. In the illustrated embodiment, the hub 562 and the boss 566 are aligned with the rotational axis 422. The braking assembly 558 includes a sleeve 570 positioned around the boss 566 and a spring washer 574 positioned between the sleeve 570 and the hub 562. A fastener 578 secures the sleeve 570 to the boss 566 and the sleeve 570 is adjustably positioned relative to the hub 562 on the user input wheel 386. In the illustrated embodiment, the fastener 578 is a screw. Adjusting the fastener 578 to position the sleeve 570 closer to the hub 562 applies a larger compressive force to the spring washer 574 and creates more frictional resistance to rotation of the user input wheel 386. Likewise, adjusting the fastener 578 to position the sleeve 570 further from the hub 562 reduced the compressive force on the spring washer 574 and reduces the frictional resistance to rotation of the user input wheel 386.

Figure 25:
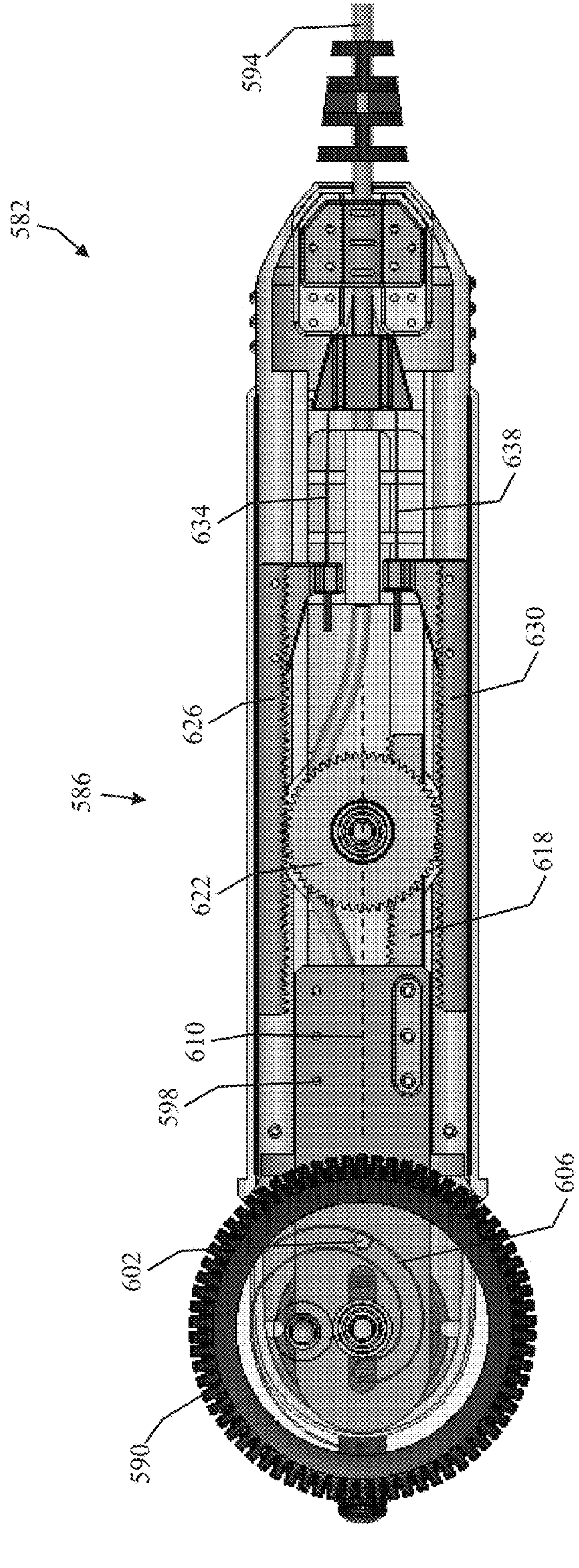
FIG. 25 is a side view of a steerable sheath with a transmission, with portions shown transparently.

With reference to FIG. 25, a steerable sheath 582 is illustrated with a transmission 586 coupled between a user input wheel 590 and a distal end of a sheath 594. The transmission 586 includes a linkage 598 coupled to the user input wheel 590 with a pin 602 received within a corresponding spiral slot 606. In the illustrated embodiment, the pin 602 moves within the spiral slot 606 in response to rotation of the user input wheel 590. The linkage 598 translates linearly along an axis 610 in response to rotation of the user input wheel 590. In the illustrated embodiment, a rack 618 is coupled to the linkage 598 and the rack 618 is enmeshed with a pinion 622. Rotation of the pinion 622 causes linear translation of a first rack 626 and a second rack 630. Similar to the transmission 402, pull wires 634, 638 are coupled to the racks 626, 630 and actuation of the pull wires 634, 638 articulates the distal end of the sheath 594.

Figure 26:
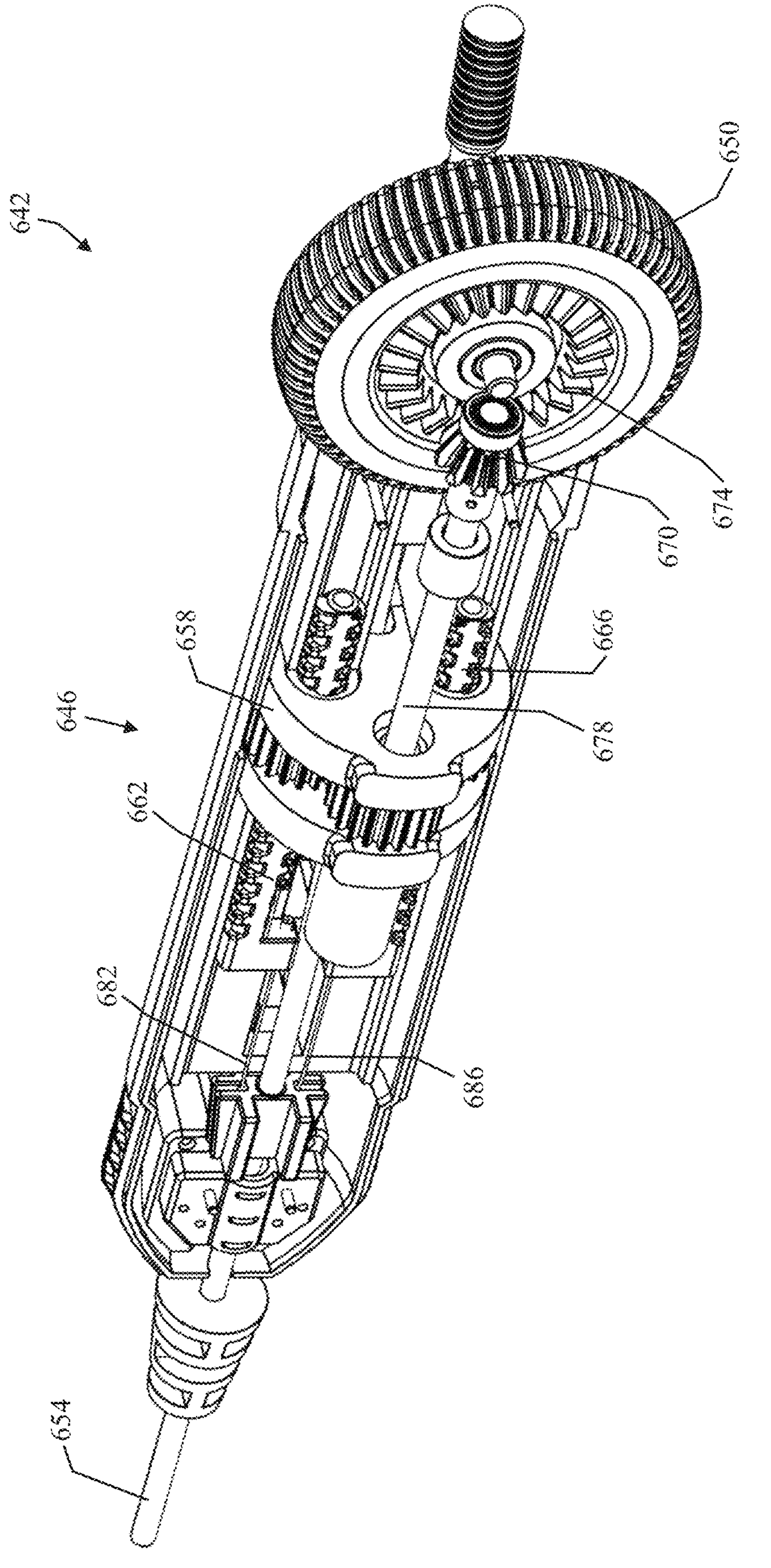
FIG. 26 is a perspective view of a steerable sheath with a transmission, with portions removed for clarity.

With reference to FIG. 26, a steerable sheath 642 is illustrated with a transmission 646 coupled between a user input wheel 650 and a distal end of a sheath 654. The transmission 646 includes a planetary gear assembly 658, a first power screw 662, and a second power screw 666. A bevel gear 670 is enmeshed with gearing 674 formed on the user input wheel 650. A shaft 678 extending from the bevel gear 670 extends into the planetary gear assembly 658 and transfers rotation from the user input wheel 650 to the planetary gear assembly 658. The power screws 662, 666 are coupled to the planetary gear assembly 658 and translate linearly in response to rotation of the user input wheel 650. In the illustrated embodiment, pull wires 682, 686 are coupled to the power screws 662, 666 and actuation of the pull wires 682, 686 articulates the distal end of the sheath 654.

Figure 27:
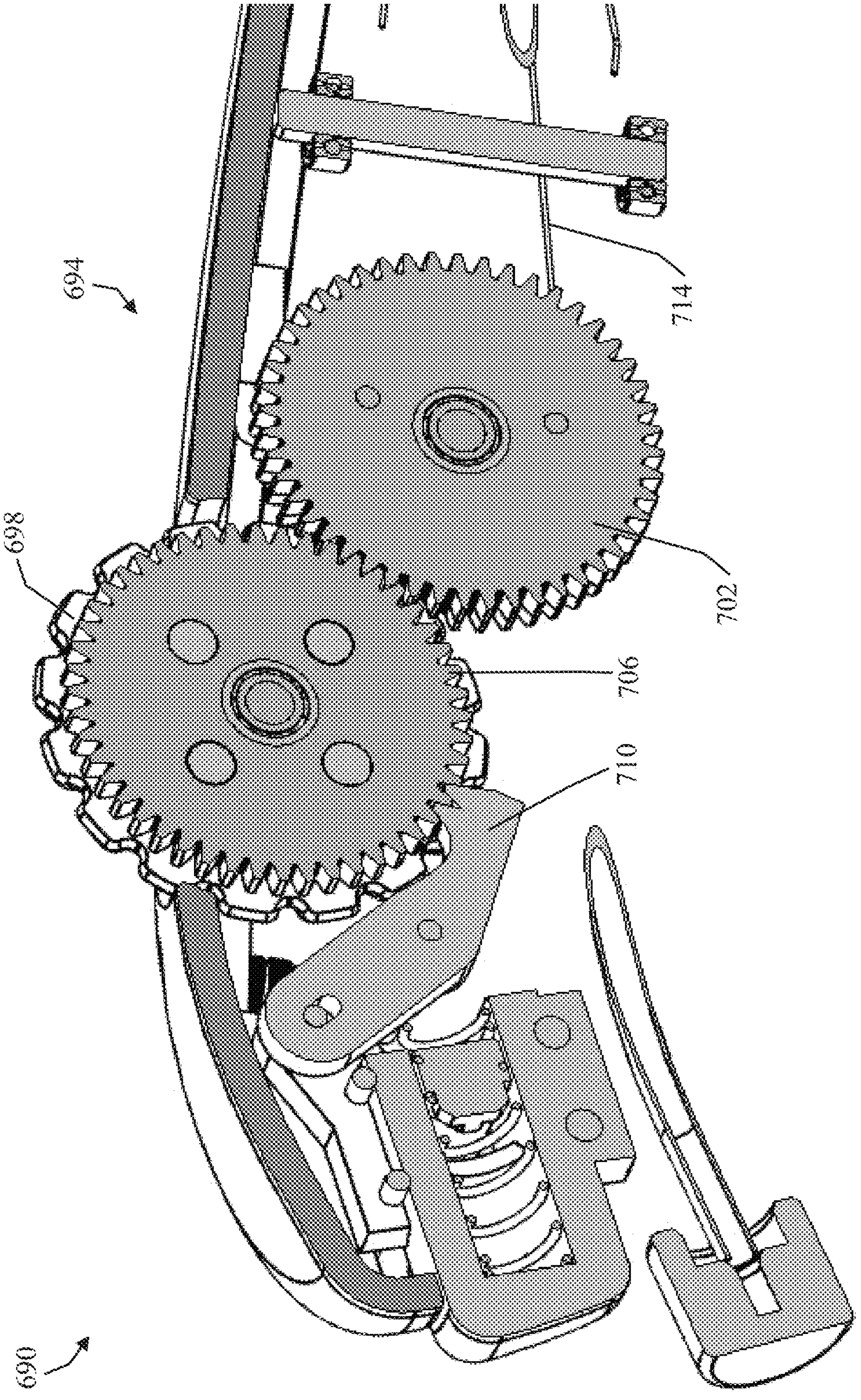
FIG. 27 is a partial perspective cross-sectional view of a steerable sheath with a transmission, with portions removed for clarity.

With reference to FIG. 27, a steerable sheath 690 is illustrated with a transmission 694 coupled between a user input wheel 698 and a distal end of a sheath. The transmission 694 includes drive gear 702 enmeshed with gearing 706 formed on the user input wheel 698 and a pawl 710 selectively engaged with the gearing 706 to lock the user input wheel 698 in position. In the illustrated embodiment, pull wires 714 are coupled to the drive gear 702 and actuation of the pull wires 714 articulate the distal end of the sheath.

In some embodiments, the transmission of the steerable sheath includes at least one electrical component (e.g., a sensor, an actuator, a power source, a controller, etc.). Advantageously, including an electrical component within the transmission may increase the precision with which the pull wires are actuated and correspondingly the precision with which the distal end of the sheath is actuated.

Figure 28:
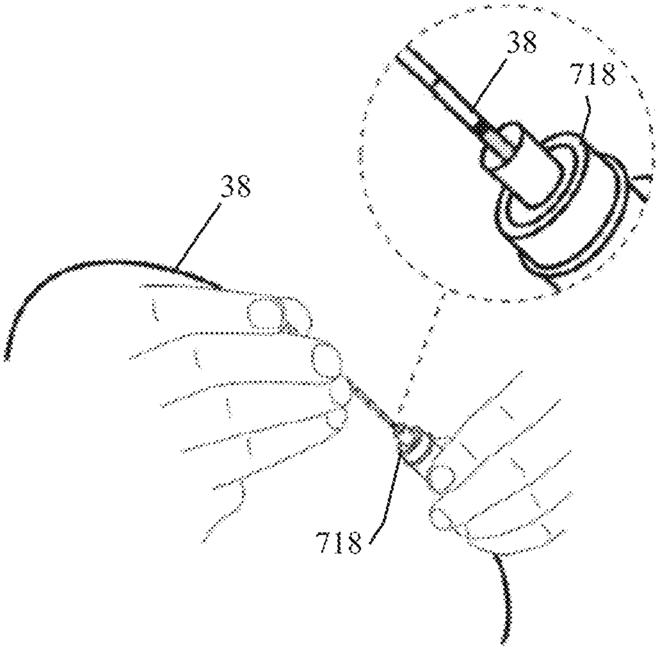
FIG. 28 is a perspective and enlarged view of a flexible probe being inserted into a sheath.

With reference to FIG. 28, in some embodiments, the flexible probe 38 is inserted into a working channel 718 (i.e., into a steerable sheath or a bronchoscope) manually with an operator feeding the flexible probe 38 into the working channel by hand. However, conventional techniques can cause the flexible probe 38 to bend, buckle, kink, or otherwise damage the flexible probe 38 in response to manually feeding the flexible probe 38 into the working channel. For example, the anatomy of the patient, or the positioning of the scope or the steerable sheath may make it difficult to feed in the flexible probe 38. In particular, there are high forces associated with the probe tip exiting the end of the working channel and pushing into tissue or a lesion. These high forces can result in undesirable buckling, bending, and/or kinking of the flexible probe 38, which can damage the flexible probe 38. As a result, conventional techniques require the user to "choke up" as much as possible on the probe and use very short advancement strokes to reduce the unsupported length of the probe.

Figure 29:
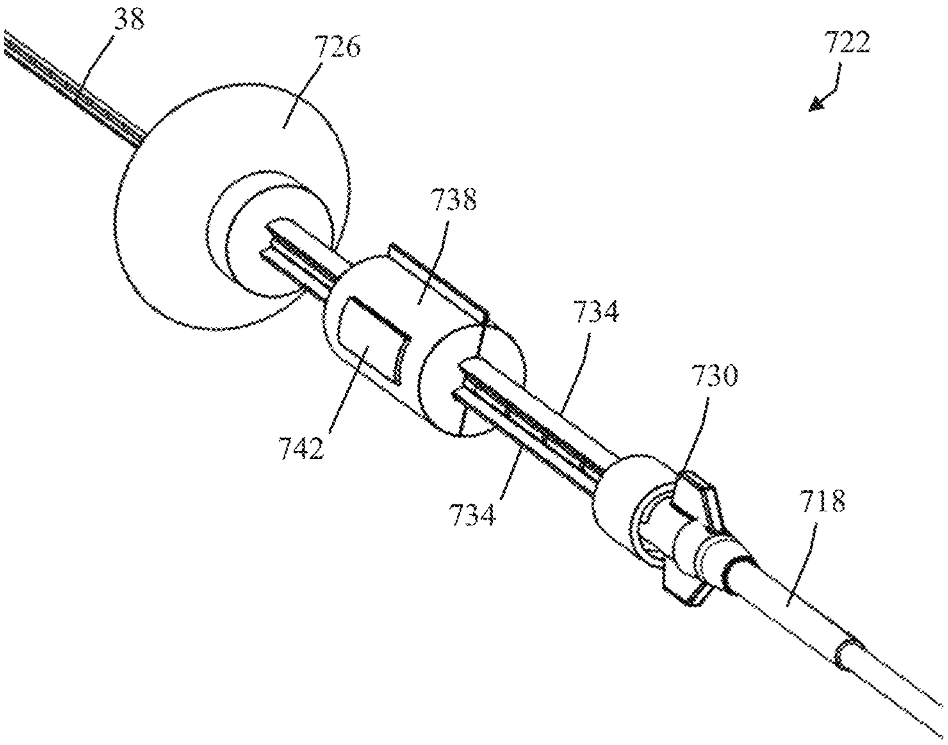
FIG. 29 is a perspective view of an anti-buckling device coupled to a flexible probe being inserted into a sheath.
Figure 30:
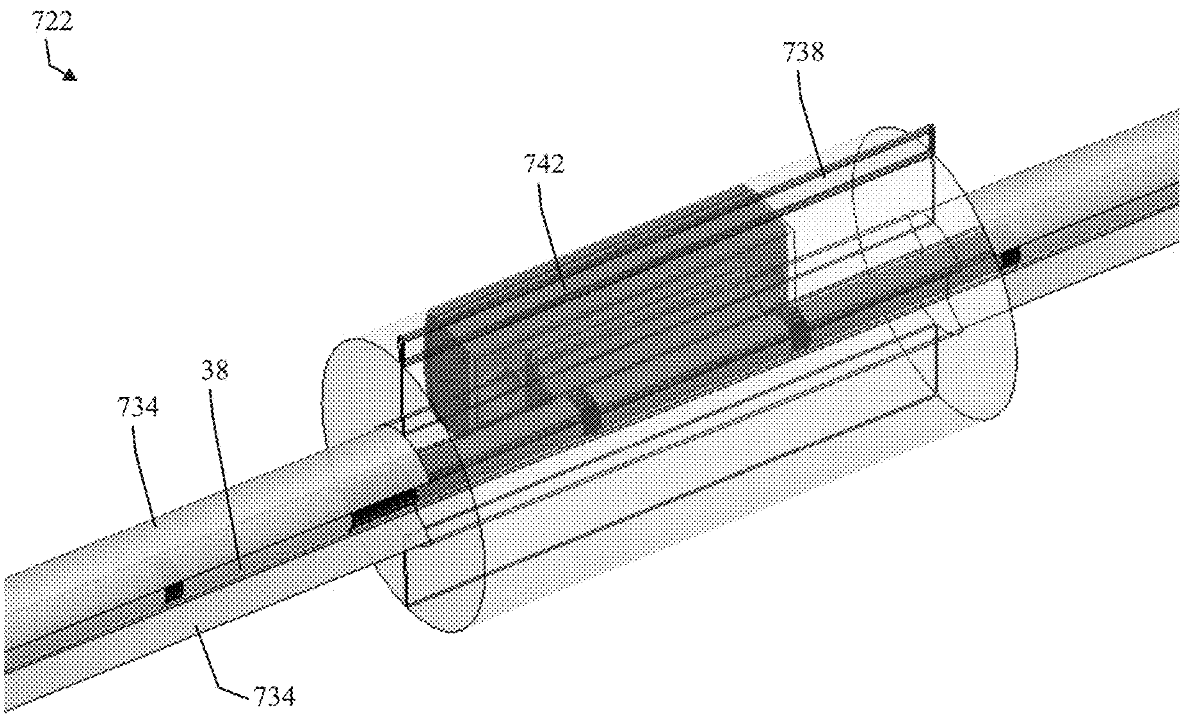
FIG. 30 is a partial perspective view of the anti-buckling device of FIG. 29, with portions shown transparently for clarity.

With reference to FIGS. 29-30, an anti-buckling device 722 is illustrated to assist with the insertion of the flexible probe 38 into the working channel 718. The anti-buckling device 722 includes an inlet funnel 726, an outlet 730, and a plurality of support rails 734 extending between the inlet funnel 726 and the outlet 730. In the illustrated embodiment, there are two support rails. In some embodiments, the outlet 730 includes a threaded luer-lok attachment. The flexible probe 38 is inserted through the inlet funnel 726 and out of the outlet 7360 into the working channel 718. In the illustrated embodiment, a portion of the flexible probe 38 is visible to an external viewer in the space between the support rails 734. In some embodiments, the anti-buckling device 722 is integrated with the working channel 718

The anti-buckling device 722 further includes a collar 738 slidable with respect to the support rails 734 and selectively coupled to the flexible probe 38. The collar 738 includes a button 742 that selectively engages the flexible probe 38 upon actuation of the button 742 by an operator. In the illustrated embodiment, the button 742 is biased by a biasing member toward a disengaged position in which the button 742 does not contact the flexible probe 38 and the collar 738 is movable with respect to the flexible probe 38. A user depresses the button 742 to move the button 742 into an engaged position in which the button 742 abuts the flexible probe 38, locking the flexible probe 38 with the collar 738 such that movement of the collar 738 moves the flexible probe 38. In some embodiments, the button 742 may be lockable in the engaged position. Releasing the button 742 from the engaged position allows the button 742 to move back to a disengaged position, such that the collar 738 is movable with respect to the probe 38. In some embodiments, the button or the collar also engage the support rails 734 in addition to the probe, thus locking the position of the probe relative to the working channel.

The flexible probe 38 is also able to move relative to the anti-buckling device 722 by manually sliding the flexible probe 38. In other words, the user has the option of using the collar 738 or their hands to translate the flexible probe 38. In some embodiments, the anti-buckling device is hinged open with two pieces that lock together such that it can be placed after the probe is already with in the working channel (i.e., the anti-buckling device) does not need to be in place prior to probe placement and therefore the probe does not need to be advanced through it initially).

Various features and advantages are set forth in the following claims.

What is claimed is:

1. A steerable sheath comprising:
- a handle, including:
  - a housing comprising a first housing portion and a second housing portion couplable to the first housing portion to define a gap therebetween, wherein the first housing portion comprises a boss extending into the gap;
  - a port formed on the housing; and
  - a user input wheel positioned in the gap and including a hub to receive the boss, thereby rotatably coupling the user input wheel to the housing;
- a sheath extending from the handle, the sheath includes a proximal end coupled to the handle and a distal end;
- a transmission coupled between the user input wheel and the distal end of the sheath;
- wherein actuation of the user input wheel articulates the distal end of the sheath.

2. The steerable sheath of claim 1, wherein the distal end is curved at an angle with the user input wheel in a neutral position.

3. The steerable sheath of claim 2, further including a detent positioned within the housing, the detent engages the transmission with the user input wheel in the neutral position.

4. The steerable sheath of claim 1, wherein the user input wheel includes a first indicator visible when the user input wheel is in the neutral position and a second indicator visible when the user input wheel is in a non-neutral position.

5. The steerable sheath of claim 1, further comprising a braking assembly that adjusts the amount of frictional engagement between the housing and the user input wheel.

6. The steerable sheath of claim 5, wherein the braking assembly includes:
- a sleeve positioned around the boss;
- a spring washer positioned between the sleeve and the hub; and
- a fastener to secure the sleeve to the boss, wherein the sleeve is adjustably positioned relative to the hub, and
- wherein the braking assembly holds the position of the user input wheel when the user input wheel is released by a user.

7. The steerable sheath of claim 1, wherein the port is connected to the sheath, and wherein an obturator is inserted through the port.

8. The steerable sheath of claim 1, wherein the user input wheel rotates about an axis, wherein the axis intersects a sheath axis, and wherein a longitudinal axis of the handle is aligned with the sheath axis.

9. The steerable sheath of claim 1, wherein the handle includes a circumferential groove on an external surface of the housing, and wherein the housing includes a tapered end, the proximal end of the sheath is coupled to the tapered end.

10. The steerable sheath of claim 1, wherein the transmission includes:
- a drive gear;
- a belt coupled between the user input wheel and the drive gear;
- a first rack enmeshed with the drive gear;
- a second rack enmeshed with the drive gear; and
- a first pull wire coupled to the first rack;
- wherein actuation of the first pull wire articulates the distal end of the sheath.

11. The steerable sheath of claim 10, wherein the transmission further includes a second pull wire coupled to the second rack; wherein actuation of the second pull wire articulates the distal end of the sheath.

12. The steerable sheath of claim 10, wherein the first rack and the second rack translate relative to the drive gear in response to rotation of the user input wheel; and
- wherein the housing includes a first slot that at least partially receives the first rack and a second slot that at least partially receives the second rack, such that the first rack and the second rack are slidable with respect to the housing.

13. The steerable sheath of claim 1, wherein the user input wheel is positioned within the handle with a first exposed portion and a second exposed portion, wherein the housing is positioned between the first exposed portion and the second exposed portion.

14. The steerable sheath of claim 1, wherein the user input wheel is rotatably coupled to the housing about an axis aligned with a longitudinal axis of the housing, wherein the user input wheel is an actuation ring.

15. The steerable sheath of claim 1, wherein the user input wheel is spaced from a proximal end of the housing.

16. The steerable sheath of claim 1, wherein the transmission includes a linkage coupled to the user input wheel with a pin and a spiral slot, and wherein the linkage translates linearly in response to rotation of the user input wheel.

17. The steerable sheath of claim 1, wherein the transmission includes a planetary gear assembly and a power screw.

18. The steerable sheath of claim 1, wherein the transmission includes a pawl.

19. The steerable sheath of claim 1, wherein the transmission includes at least one electrical component, wherein the electrical component is a sensor, an actuator, a power source, or a controller.

20. A steerable sheath, comprising:
- a housing comprising a first housing portion and a second housing portion couplable to the first housing portion to define a gap therebetween, wherein the first housing portion comprises a boss extending into the gap;
- a user input wheel positioned in the gap and including a hub to receive the boss, thereby rotatably coupling the user input wheel to the housing; and
- a sheath extending from the handle, wherein rotation of the user input wheel about the boss articulates the sheath.

* * * * *